US005727335A

United States Patent [19]
Kousaka et al.

[11] Patent Number: 5,727,335
[45] Date of Patent: Mar. 17, 1998

[54] FOOTWEAR FOR PATIENTS OF OSTEOARTHRITIS OF THE KNEE

[75] Inventors: Sachiko Kousaka; Mitsuko Kousaka, both of Sakai; Kumiko Isaka, Izumi, all of Japan

[73] Assignee: Limited Responsibility Company Frontier, Osaka, Japan

[21] Appl. No.: 711,056

[22] Filed: Sep. 9, 1996

Related U.S. Application Data

[62] Division of Ser. No. 268,176, Jun. 29, 1994, Pat. No. 5,579,591.

[30] Foreign Application Priority Data

| Jun. 29, 1993 | [JP] | Japan | 5-185462 |
| Jul. 18, 1993 | [JP] | Japan | 5-198974 |
| Aug. 9, 1993 | [JP] | Japan | 5-217041 |
| Sep. 14, 1993 | [JP] | Japan | 5-252260 |
| Nov. 22, 1993 | [JP] | Japan | 5-316015 |
| Apr. 21, 1994 | [JP] | Japan | 6-107764 |
| May 26, 1994 | [JP] | Japan | 6-136338 |
| Jun. 27, 1994 | [JP] | Japan | 6-145090 |

[51] Int. Cl.⁶ ............... A43B 13/14; A61F 5/14
[52] U.S. Cl. ............... 36/31; 36/30 R; 36/25 R; 36/140
[58] Field of Search ............... 36/110, 30 R, 36/32 R, 28, 91, 25 R, 31, 140

[56] References Cited

U.S. PATENT DOCUMENTS

| 2,071,431 | 8/1937 | Riddell | 36/14 |
| 2,424,463 | 6/1947 | Hogg | 36/59 |
| 3,566,487 | 3/1971 | Beightol | 36/2.5 |
| 3,918,181 | 11/1975 | Inohara | 36/2.5 A |
| 4,316,332 | 2/1982 | Giese et al. | 36/28 |
| 4,316,336 | 2/1982 | Giese et al. | 36/129 |
| 4,348,821 | 9/1982 | Daswick | 36/103 |
| 4,354,319 | 10/1982 | Block et al. | 36/114 |
| 4,364,188 | 12/1982 | Turner et al. | 36/31 |
| 4,372,059 | 2/1983 | Ambrose | 36/32 R |
| 4,425,721 | 1/1984 | Spronken | 36/11.5 |
| 4,757,620 | 7/1988 | Tiitola | 36/28 |
| 4,887,367 | 12/1989 | Mackness et al. | 36/28 |
| 5,042,174 | 8/1991 | Nichols | 36/25 R |
| 5,077,915 | 1/1992 | Gross | 36/31 |
| 5,088,481 | 2/1992 | Darby | 36/102 |
| 5,138,777 | 8/1992 | Darby | 36/88 |

Primary Examiner—Ted Kavanaugh
Attorney, Agent, or Firm—Leydig, Voit & Mayer, Ltd

[57] ABSTRACT

Footware is made such that a thickness of a heel region from a sole upper surface to the ground is thinner at a backward portion than at a forward portion, whereby a line connecting a position on a lower surface of the sole under the head of the second metatarsus to a front end on a lower surface of the heel region of the sole is lifted at an angle with a horizontal line connecting a grounded rear end on the lower surface of the heel region to a front end thereof in a state where a weight is loaded to the human heel, and the backward portion of the heel region comprises an impact absorbing mechanism, whereby a level of the human heel which is in contact with a foot is depressed when loaded. Thus, the footwear protects a knee joint of a patient suffering from the osteoarthritis of the knee and enables them to easily walk.

12 Claims, 18 Drawing Sheets

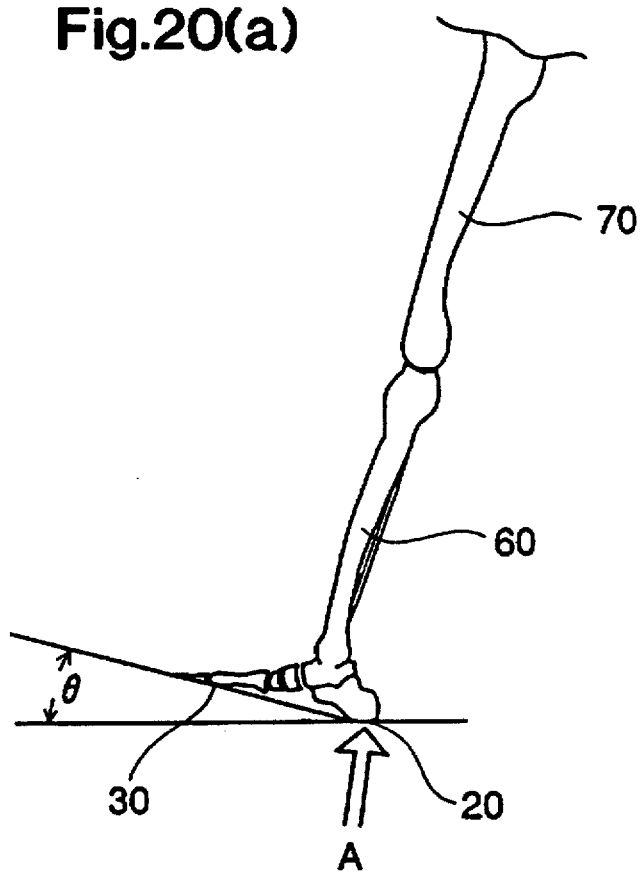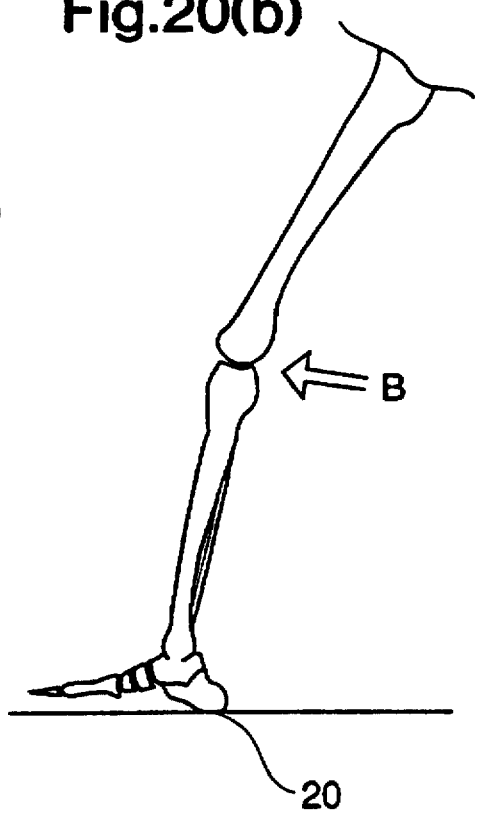
Fig.20(a)
Fig.20(b)

FOOTWEAR FOR PATIENTS OF OSTEOARTHRITIS OF THE KNEE

This disclosure is a division of patent application Ser. No. 08/268,176, filed Jun. 29, 1994 now U.S. Pat. No. 5,579,591.

[INDUSTRIAL FIELD OF UTILIZATION]

The present invention relates to footwear for patients suffering from osteoarthritis of the knee and more particularly, to footwear for patients suffering from the osteoarthritis of the knee, which has a sufficient function as the footwear for the above patients but does not look strange because of that function, and which looks normal apparently and can be easily put on.

[PRIOR ART]

Among footwear regarded as being effective to a disease of knee joint, there is a shoe having an extremely low heel in a sole 102 is shown in a conventional example 1 in FIG. 18. According to explanation of the shoe, which is an effective shoe for patients whose muscular strength of legs is so lowered that walking is peculiar. However, the shoe is not suitable for general patients except for the above patients. In addition, since the shoe causes a habit such that the Achilles' tendon is stretched because the shoe fails in "third state" shown in FIG. 2(b) to be described later. If the shoes are habitually used, the Achilles' tendon is stretched and a stretching effect ("knee stretching effect" to be described later) is declined. Additionally, the patients have difficulty in walking on the shoes. Still further, because of the above-mentioned habit, a rear part of a heel region cannot be set at an angle enough to secure an initial purpose, and it cannot avoid being at a small angle.

Meanwhile, in another example, there is a shoe shown in a conventional example 2 in FIG. 19, which is for training the muscle. However, a configuration of the shoe is not normal and since force is unnaturally applied to stretch the knee, it trains the muscle but there is a note that it should not be used for a sick person. More specifically, this shoe is intended for healthy people who want to train their muscles and it is no good for the sickly person to wear the shoes.

Furthermore, although a conventional example 3 is not shown, it is generally called a rocker shoe whose sole is in form of circular arc. This kind of shoe protects an ankle part but unstable in the front-to-rear direction because a grounding point varies in the front-to-rear direction (because of shift of a supporting point). Thus, the shoe exerts a bad influence on the knee of the patients suffering from the osteoarthritis of the knee, who is an object of the present invention.

Still further, the inventors of the present invention already disclosed a shoe which has a function superior to the above-mentioned conventional examples, in Japanese Patent Laying Open No. 107243/1990. That application is as follows.

When a person walks and a heel lands on the ground, an angle θ is formed between the ground and a line connecting the heel and the sole as shown in FIG. 20(a), so that the calcaneus is pushed up (in a direction shown by an arrow A) by an impact of the landing and a rotation force around an ankle is generated. Thus, the knee is bent (moved in a direction shown by an arrow B) as shown in FIG. 20(b). Such a phenomenon in which the knee is pushed up from the calcaneus and bent each step is called a "natural impact absorbing function" given to a human being in one aspect.

The force resisting the force in the direction of the arrow A is a spring of the calcaneus and the force resisting the force in the direction of the arrow B is a spring of the knee. However, in another-aspect, the force received by the springs (in the directions of the arrows of A and B) badly influence the knee joint of the patients of the osteoarthritis of the knee. The above phenomenon (forces in the directions of the arrows of A and B) is referred to as a "bending action of the knee by the calcaneus" hereinafter.

While the knee is repeatedly bent (that is, moved) each step, the knee joint of the patient of the osteoarthritis of the knee is worn away. In order to solve the problem, according to Japanese Patent Laying Open No. 107243/1990 by the inventors of the present invention, as shown in FIG. 17, a substantial heel rear end E is disposed in the vicinity of a vertical line. x—x and a region behind the heel end is cut out. Thus, when the person walks and then, the heel lands on the ground, the calcaneus is prevented from being pushed upward (in the direction of the arrow A) by the impact of the landing as shown in FIG. 20, whereby the knee is prevented from being bent in the direction of the arrow B. Thus, if the patient can walk without bending the knee and the heel can land on the ground without repeatedly bending the knee each step, the disease of the knee joint can be healed and at least worsening of the disease can be stopped. The effect obtained by landing the heel without bending the knee joint is called a "knee joint non-bending effect".

As described above, according to the above shoe of the previous application by the inventors of the present invention, since the substantial heel rear end E is disposed close to the vertical line x—x and the region behind the heel rear end E is cut out so as not to protrude from a line A—A as shown in FIG. 17, the cut-out surface becomes a long inclined surface. Since an angle ρ of inclination can not be reduced in order to keep a stride of the person constant, the heel becomes high. If the angle ρ of inclination is reduced (for example, to 15 degrees) in order to avoid the high heel, in a case of landing with a heightened toe by the angle of θ as shown in FIG. 20(a) or the ground is a gentle downhill, the heel end directly receives the force in the direction shown by the arrow A and the diseased part is worsened. Therefore, it is necessary to additionally increase the angle ρ (for example, 30 degrees) with due regard to the case of landing with a heightened toe or landing on the downhill ground, which means that the heel is heightened. Thus, as the heel is heightened, the lower end b of the calcaneus protrudes backward.

The phenomenon in which the calcaneus protrudes backward will be described according to the drawings. When the conventional high-heeled shoe (shown in FIG. 21) is compared with the extremely low-heeled shoe (shown in FIG. 22), as the heel is heightened, a lower end a of the calcaneus protrudes backward along an arc 103 around an ankle 50. The backward protrusion of the calcaneus lower end a is a characteristic of the high-heeled shoe, which is largely different from a calcaneus lower end c in the low-heeled shoe. The phenomenon in which the calcaneus lower end a on the general high-heeled shoe protrudes backward more than the calcaneus lower end c on the low-heeled shoe is called a "backward protrusion phenomenon of the calcaneus" hereinafter.

FIG. 23 shows a relation between the above "backward protrusion phenomenon of the calcaneus" and a height of the calcaneus. Referring to FIG. 23, a distance between the calcaneus lower end (the farthest calcaneus end from the ankle) a, b or c and the vertical line x—x is a function of the height of the heel. More specifically, the following equation is concluded.

$$D = R \sin \alpha$$

where D is a distance between points a, b or c positioned along the arc 103 and the vertical line x—x, which is regarded as a height of a right triangle assuming that a distance R1, R2 or R3 between the ankle 50 of the rotation axis and the calcaneus lower end a, b or c, respectively is the hypotenuse and the line x—x is the base. Thus, as the heel is heightened, the distance D is increased. Therefore, the distance D is changed to D1, D2 and D3 as the height of the heel is lowered. The distance D may be regarded as a rotation moment applied to the rotation axis 50. Therefore, a rotation force applied to the rotation axis 50 in the position a in the case of high heel shown in FIGS. 23 and 21 is much greater than that in the position c in the case of extremely low heel shown in FIGS. 23 and 22, and the above-described defect, that is, the "knee bending action by the calcaneus" is worsened as the heel is heightened. Although it is a matter for regret, since one disclosed in the previous application shown in FIG. 17 is also a high-heeled shoe, the calcaneus lower end b largely protrudes backward as shown in FIG. 17 like the general high-heeled shoe (shown in FIG. 21) so that the calcaneus is pushed upward (in the direction shown by the arrow A) as described in FIG. 20 by the protrusion. However, in order to secure the above-described angle ρ(shown in FIG. 17), the heel is high and the calcaneus end is positioned at b shown in FIG. 23. Thus, as the heel is heightened, the above-described defect, that is, the "backward protrusion phenomenon of the calcaneus" can not been avoided.

In addition, the shoes shown in FIGS. 17, 18 and 19 look strange because of their particular function.

Additionally, as an example of the osteoarthritis of the knee, there are varus (bandy leg) and valgus (knock knee). In order to ease or cure the above condition of the patient, there is used a method in which inclination is formed inside the sole of the shoe so that the inside (or outside) of the joint to be particularly protected is kept low. However, the osteoarthritis of the knee is not likely to be cured only by forming the inclined surface in the sole of the shoe and the troubles of the patients are not solved at the present.

[SUMMARY OF THE INVENTION]

The present invention was made to solve the above problems and it is an object of the present invention to provide footwear which enables patients of osteoarthritis of the knee to walk easily, looks normal and can be easily put on even indoors.

According to the present invention, a footwear body comprises an upper and a sole, and a heel region having a thickness from a sole upper surface to the ground. The thickness is formed thinner at a backward portion than at a forward portion, whereby a line connecting a position on a lower surface of the sole under the head of the second metatarsus to a front end on a lower surface of the heel region of the sole is lifted at an angle with a horizontal line connecting a grounded rear end on the lower surface of the heel region to a front end thereof in a state where a weight is loaded to a human heel, and the backward portion of the heel region comprises an impact absorbing mechanism, whereby a level of the heel portion which is in contact with a foot is depressed when loaded. Thus, a "supporting effect close to the vertical line" is obtained by lifting the lower surface of the sole under the head of the metatarsus from the horizontal line at the time of landing. This effect enables to prevent the "calcaneus backward projecting phenomenon", and reduce a "knee bending action by the calcaneus" in which the calcaneus is pushed upward and the knee is bent at the moment of the landing. In addition, in order to compensate loss of a "natural impact absorbing function" which is naturally given to a human being and generated from the above action, there is provided the impact absorbing mechanism. As a result, the loss of the "natural impact absorbing function" can be compensated and the toe is further lifted by depression of the human heel, which can generate a "knee stretching effect".

In addition, according to footwear for patients suffering from the osteoarthritis of the knee according to the present invention, the lifted angle formed by the lower surface of the sole under the head of the second metatarsus with the ground is at least 5 degrees in a state where the human heel receives a load of 70 kg. Therefore, the "knee bending action by the calcaneus" can be reduced.

In addition, according to footwear for patients suffering from the osteoarthritis of the knee according to the present invention, the impact absorbing mechanism comprises a human heel supporting elastic member or an inner member in the shoe which is positioned under the human heel and whose at least one part is made of a material which is easily elastically deformed when loaded from the human heel, and the surface of the inner member which is in contact with the human heel is depressed by the elastic deformation. Therefore, the "natural impact absorbing function" can be compensated.

In addition, according to footwear for patients suffering from the osteoarthritis of the knee according to the present invention, the sole and heel region form a balance member comprising a lower support positioned at the front end of the heel region and a longitudinal member positioned above the lower support. Thus, the weight can be supported in balance and it can be transferred by a small load.

In addition, according to footwear for patients suffering from the osteoarthritis of the knee according to the present invention, the balance member has a length in the horizontal direction substantially ranging from the human heel to the head of the metatarsus, whereby the weight is received at positions of the head of the metatarsus and the human heel and supported by the lower support in balance. Thus, the weight can be supported in balance and the above action can be ensured.

In addition, according to footwear for patients suffering from the osteoarthritis of the knee according to the present invention, the lower support is positioned at a place of 41% to 65% of the total length of the shoe body from the rear end of the shoe body along the second metatarsus. Thus, the balance member has the balancing function and the above action can become more effective.

In addition, according to footwear for patients suffering from the osteoarthritis of the knee according to the present invention, the lower support forms a ridgeline crossing a bottom surface of the sole, and an interval between the ridgeline and the rear end of the heel is longer on the fifth toe than on the first toe when it is measured in parallel with a line connecting the head of the second metatarsus and the center of the calcaneus. Thus, especially the condition of bandy leg or the like can be cured.

In addition, according to footwear for patients suffering from the osteoarthritis of the knee according to the present invention, a configuration of a bottom of the sole between the sole lower surface under the head of the second metatarsus and the lower support is substantially in line or bent upward in its side view when loaded. Thus, the lower support can be prevented from shifting while the weight is transferred.

In addition, according to footwear for patients suffering from the osteoarthritis of the knee according to the present invention, a configuration of a bottom of the sole between the rear end on the lower surface of the heel region and the lower support is substantially in line or bent upward in its side view when loaded. Thus, the lifted angle can be prevented from being swayed and precisely maintained.

In addition, according to footwear for patients suffering from the osteoarthritis of the knee according to the present invention, the impact absorbing mechanism having a surface which is in contact with the human heel, has a function of absorbing an impact instead of or beyond a natural function of absorbing an impact generated when the knee is bent forward by counterforce received by the calcaneus from the ground during walking. Thus, the "loss of the natural impact absorbing function" can be sufficiently compensated.

In addition, according to footwear for patients suffering from the osteoarthritis of the knee according to the present invention, elasticity of the human heel supporting elastic member can be easily deformed as compared with each member forming the balance member. Therefore, the impact absorbing mechanism and the weight supporting mechanism can be obtained.

In addition, according to footwear for patients suffering from the osteoarthritis of the knee according to the present invention, a difference in elasticity between the balance member and the human heel supporting elastic member is made by at least one of a difference in size of pores, perforations, space and concave parts, a difference in number thereof, a difference in sectional area or a difference in elasticity of materials. Therefore, the impact absorbing mechanism and the weight supporting mechanism can be obtained.

In addition, according to footwear for patients suffering from the osteoarthritis of the knee according to the present invention, the impact absorbing mechanism absorbs an impact by elastic deformation of the inner member in the shoe or the human heel supporting elastic member, and a height of a surface which is in contact with the lower end of the human heel is lowered by at least a height of 2% of the total length of the shoe when the surface is loaded by 70 kg. Therefore, the "loss of the natural impact absorbing function" can be sufficiently compensated.

In addition, according to footwear for patients suffering from the osteoarthritis of the knee according to the present invention, the impact absorbing mechanism absorbs an impact by elastic deformation of the human heel supporting elastic member and a height of the rear end of the upper surface of the sole is lowered by at least a height of 0.5% of the total length of the shoe when the human heel receives a load of 70 kg. Therefore, the "loss of natural impact absorbing function" can be compensated.

In addition, according to footwear for patients suffering from the osteoarthritis of the knee according to the present invention, at least one part of the impact absorbing mechanism is made of an impact absorbing material. Therefore, in addition to the above action, the initial impact can be absorbed at the time of landing.

In addition, according to footwear for patients suffering from the osteoarthritis of the knee according to the present invention, an inclined surface in which the left side is higher than the right side as viewed from the back side or vice versa, is formed at a bottom inside the shoe body so as to lower a diseased part of the knee joint. Therefore, alignment of each bone connected to the joint on the upper or lower side can be corrected into the direction so that the diseased side of the knee joint can be protected.

In addition, according to footwear for patients suffering from the osteoarthritis of the knee according to the present invention, the inclined surface is formed in the inner member of art elastic material which is disposed inside the shoe body. Therefore, in addition to the above action, the impact at the time of landing can be absorbed.

In addition, according to footwear for patients suffering from the osteoarthritis of the knee according to the present invention, a part of the inclined surface for supporting the human heel is formed so as to be more easily elastically deformed than another region. Therefore, in addition to the above action, the initial impact at the time of landing can be absorbed.

In addition, according to footwear for patients suffering from the osteoarthritis of the knee according to the present invention, a difference in elasticity on the inclined surface is made by at least one of a difference in size of pores, perforations, space and concave parts, a difference in number thereof, or a difference in elasticity of their materials. Therefore, a difference in elasticity for obtaining the above action can be appropriately adjusted.

In addition, according to footwear for patients suffering from the osteoarthritis of the knee according to the present invention, a difference in elasticity is made between a part supporting the lower side of the inclined surface and a part supporting the upper side thereof in the human heel supporting elastic member, whereby the part supporting the lower side is easily depressed as compared with the part supporting the upper side. Thus, in addition to the correcting action of the knee joint by the inclined surface, the accordingly generated "uneven depression phenomenon of the heel" can be prevented.

In addition, according to footwear for patients suffering from the osteoarthritis of the knee according to the present invention, a partial difference in elasticity in the human heel supporting elastic member is made by at least one of a difference in size of pores, perforations, space and concave parts, a difference in number thereof, a difference in a sectional area or a difference in elasticity of their materials. Therefore, the difference in elasticity for obtaining the above action can be appropriately adjusted.

In addition, according to footwear for patients suffering from the osteoarthritis of the knee according to the present invention, the upper is reinforced by a reinforcing material at the lower side of the inclined surface as compared with the upper on the higher side thereof in order to prevent a foot from sideslipping toward the lower side of the inclined surface. Thus, the human heel is prevented from sideslipping.

In addition, according to footwear for patients suffering from the osteoarthritis of the knee according to the present invention, a decorative heel configuration forming member which is easily elastically deformed more than the human heel supporting member is disposed behind the human heel supporting elastic member. Thus, even if the substantial heel is disposed at a specific position for obtaining the "supporting effect close to the vertical line", an appearance of the heel looks like a normal shoe.

In addition, according to footwear for patients suffering from the osteoarthritis of the knee according to the present invention, the rear end on the lower surface of the human heel supporting elastic member is positioned at a place of at least 5% of the total length of the shoe from the rear end of the shoe. Therefore, the "supporting effect close to the vertical line" can be obtained.

In addition, according to footwear for patients suffering from the osteoarthritis of the knee according to the present invention, space in each of the balance member, the human heel supporting elastic member and the decorative heel configuration forming member which are formed between the upper surface of the sole and the ground, and space between them are filled with an elastic material whose elasticity is lower than that of any of the above members. Therefore, even if the bottom covering material exists or not, the appearance can be adjusted.

In addition, according to footwear for patients suffering from the osteoarthritis of the knee according to the present invention, a decorative sole configuration forming member made of an easily elastically deformed material is disposed at the lifted bottom of the sole under the head of the second metatarsus. Therefore, the appearance can be adjusted.

In addition, according to footwear for patients suffering from the osteoarthritis of the knee according to the present invention, a rear part of the upper is not provided in the upper. Therefore, the configuration of the external appearance can be selected.

in addition, according to the footwear for patients suffering from the osteoarthritis of the knee according to the present invention, a configuration of the uppers lacking one part is close to a backless slipper. Therefore, it is easy to put on.

[BRIEF DESCRIPTION OF THE DRAWING]

FIG. 20(a) and 20(b) is a view for explaining an action of force exerted on a knee from a calcaneus.

[DETAILED DESCRIPTION OF PREFERRED EMBODIMENTS]

Embodiments of the present invention will be described hereinafter. In addition, embodiments 1 to 5 will be described according to footwear having a configuration of a shoe. An embodiment 6 will be described according to a shoe lacking a rear part of uppers. Although the footwear lacking the rear part of the uppers comprises "sandals" or the like, the footwear like slippers will be described as one example according to the embodiment of the present invention.

Embodiment 1

Figure 1:
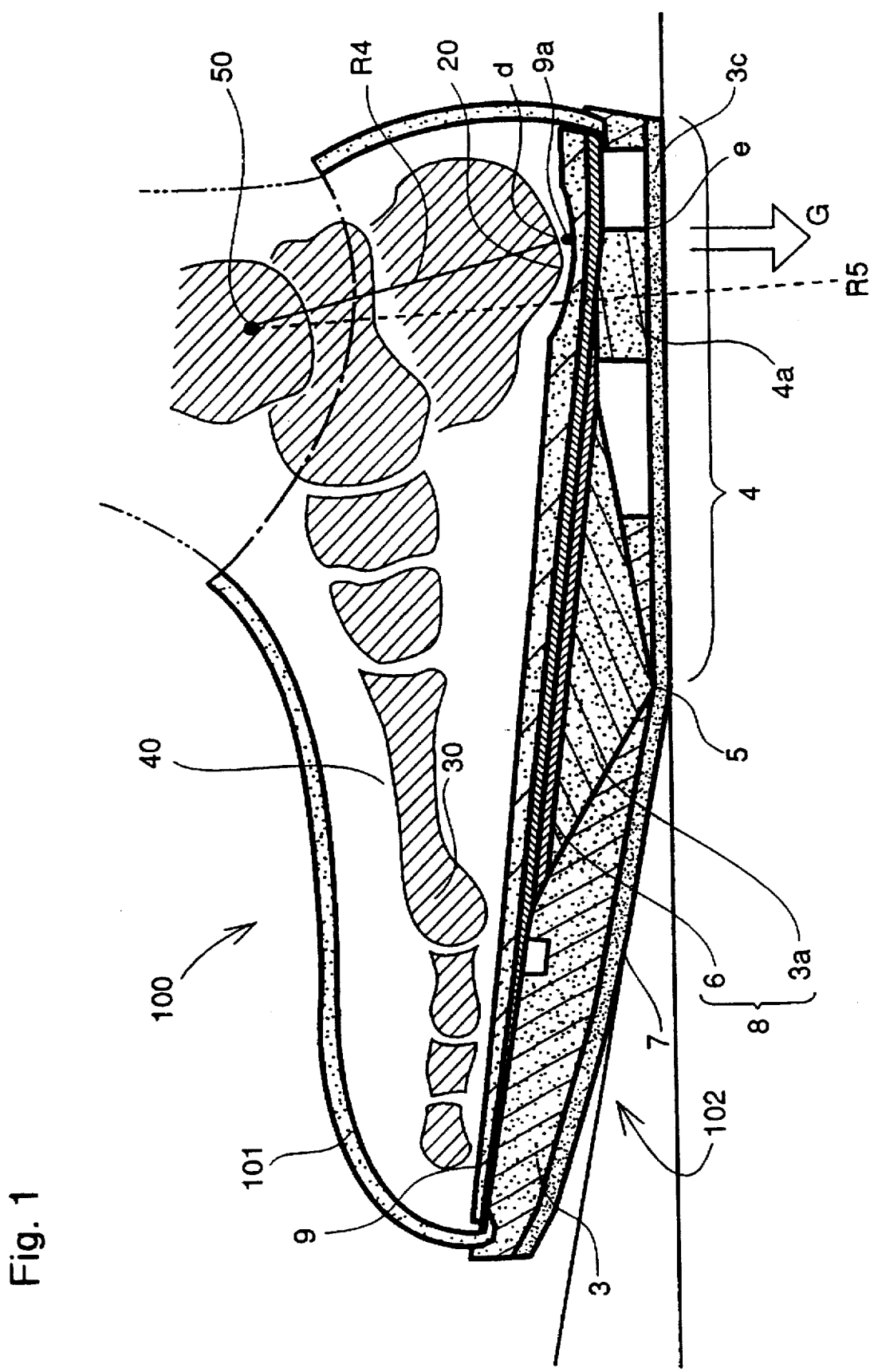
FIG. 1 is a vertical sectional view taken along line 3a—3a of FIG. 3(c) showing footwear for patients suffering from the osteoarthritis of the knee in a "first state" at the time of walking according to a first embodiment of the present invention.
Figure 2A:
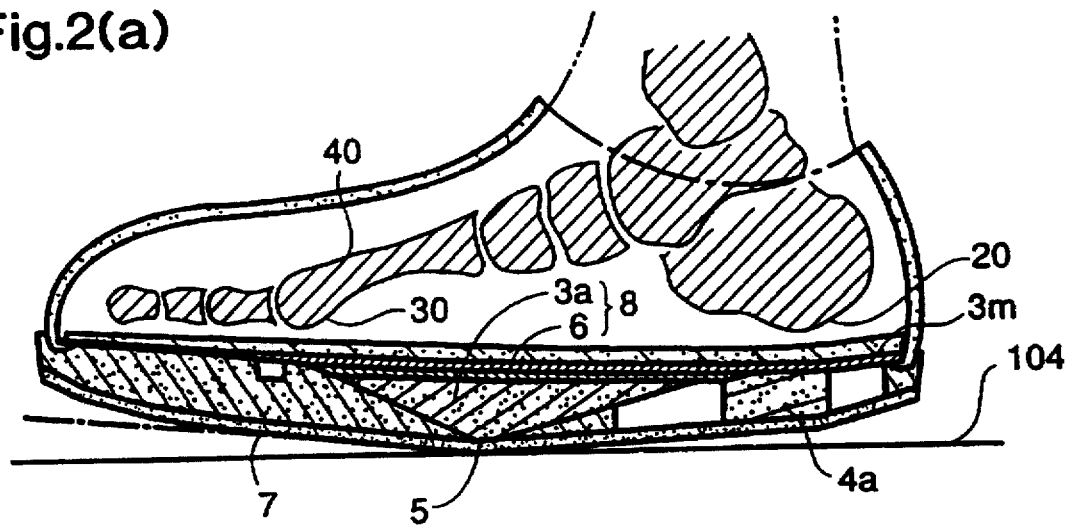
FIG. 2(a)–2(c) are vertical sectional views taken along line 3a—3a of FIG. 3 (c) showing the footwear for patients suffering from the osteoarthritis of the knee in a "second state" (FIG. 2(a)), a "third state" (FIG. 2(b)), and a "fourth state" (FIG. 2(c)) at the time of walking according to the first embodiment of the present invention.

FIGS. 1 and 2(a), (b) and (c) are views showing process of walking on a shoe for a patient suffering from the osteoarthritis of the knee according to an embodiment of the present invention. In the drawings, the process from landing to kicking out is sequentially divided into four states, that is, "first state" to "fourth state" to be described later, which is shown in section.

Figure 3A:
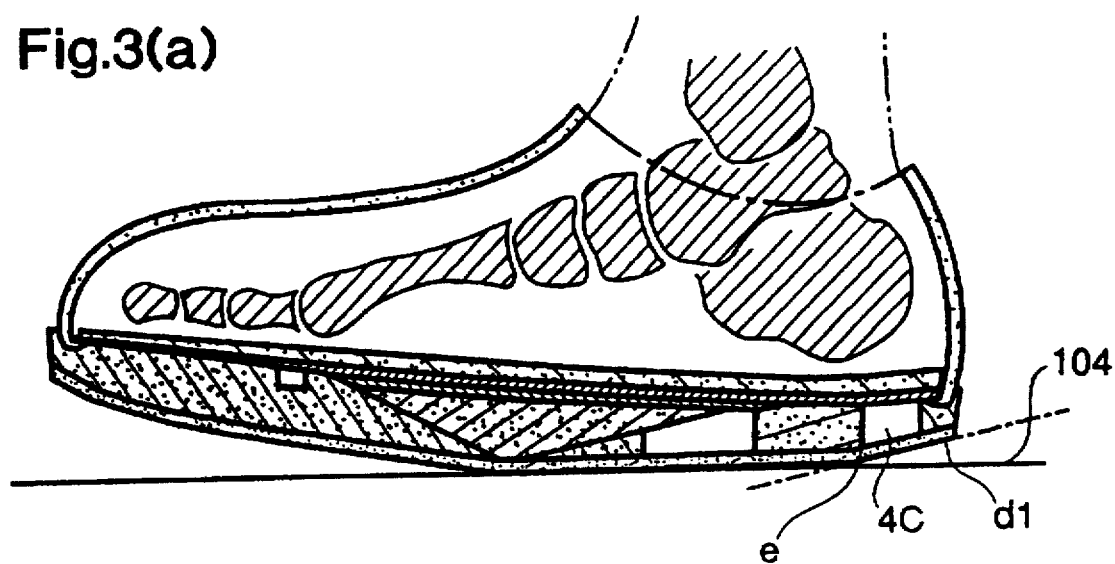
FIG. 3(a)–3(c) are a vertical sectional view taken along line 3a—3a of FIG. 3(c) (FIG. 3(a)), a side view (FIG. 3(b)), and a bottom view (FIG. 3(c)) of the footwear for patients suffering from the osteoarthritis of the knee according to the first embodiment of the present invention.
Figure 3B:
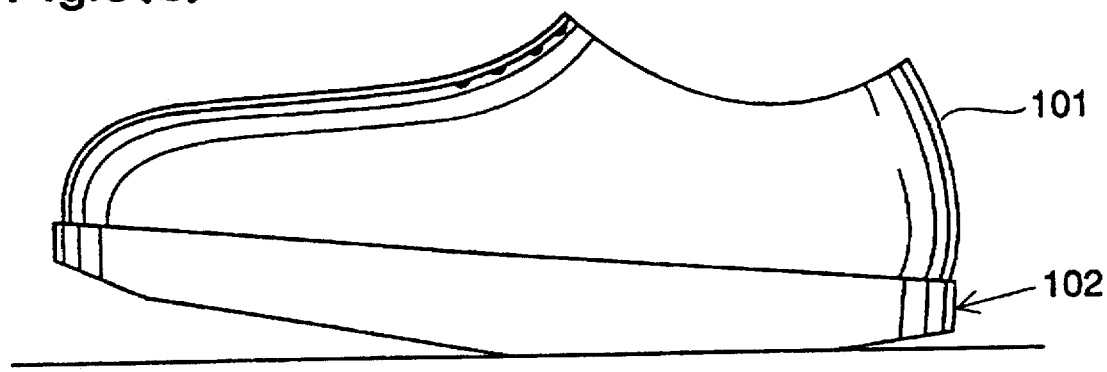
Figure 3C:
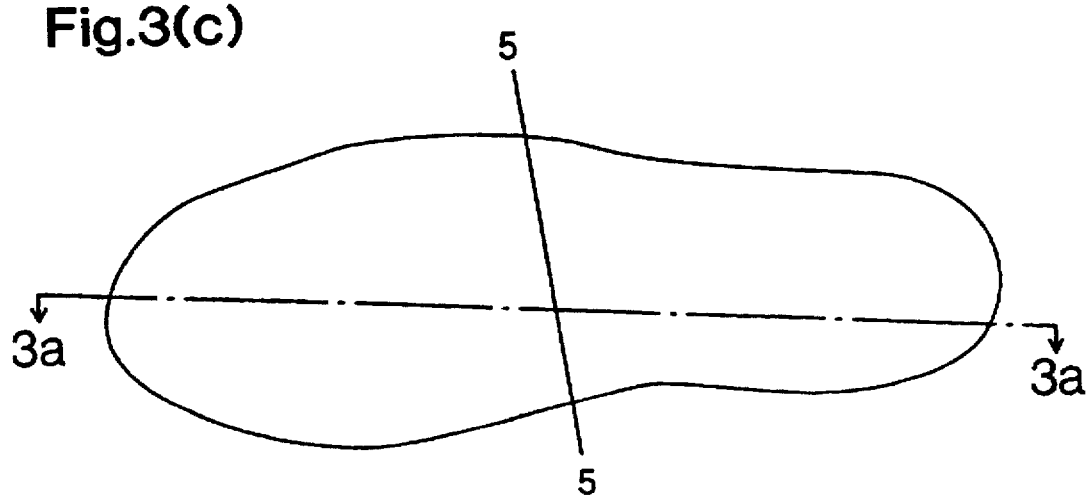

FIG. 3(a) and (b) show the shoe which is not loaded according to the embodiment 1 of the present invention, and FIG. 3(c) is a bottom view of a sole of the shoe. FIG. 3(a) is a vertical sectional view taken along a dotted line 3a—3a of FIG. 3(c), and FIG. 3(b) is a side view showing an external appearance of the shoe according to the embodiment 1.

Referring to FIG. 1, reference numeral 100 designates a shoe body, reference numeral 101 designates an upper, reference numeral 102 designates a sole, reference numeral 3 designates an elastic member at a front sole, reference numeral 4 designates a heel region from a front end of a grounding surface of the heel (a lower support to be described later) to the end of the heel, reference numeral 5 designates the lower support which supports a load like a balance in the "second state" to be described later, reference numeral 6 designates a longitudinal member serving as a balance which supports the load applied to the head of the metatarsus on the upper surface of the sole and the human heel, reference numeral 3a designates a support member formed of a material which is not likely to be elastically deformed as compared with the heel region and connecting the lower support and the longitudinal member, reference numeral 7 designates a lower surface of the sole positioned under the head of the metatarsus, and reference numeral 8 designates a balance member comprising the longitudinal member 6 and the support member 3a. In addition, reference numeral 9 designates an inner member formed in the sole, reference numeral 20 designates a calcaneus, reference numeral 30 designates a head of the second metatarsus, reference numeral 40 designates the second metatarsus, reference numeral 50 designates a center of an ankle, reference numeral 3c designates a sole covering material, reference numeral 4a designates an elastic material for supporting the human heel which is a substantial heel, reference numeral 9a designates an upper surface of the inner member 9 on which the human heel is in contact, and reference character e designates a rear end on a lower surface of the human heel supporting elastic material 4a.

Since the sole is covered with the sole covering material 3c and the inner structure shown in the sectional view is not seen from the sole, but description of the lower support 5 and the rear end e on the lower surface of the human heel supporting elastic member 4a to be described later will be made assuming that the sole covering material 3c does not exist for convenience. In its modification, the lower support 5 may be directly in contact with the ground without the sole covering material 3c, and existence of the sole covering material 3c has nothing to do with the substantial function. The sole covering material may be integrally formed with the front sole elastic member 3 and or the human heel supporting elastic member 4a to be described later. When the sole covering material 3c is omitted, since the inner structure is exposed, as will be described in an embodiment 5, space formed in each of and between the balance member 8, the human heel supporting elastic member 4a and a member 4b for forming a configuration of a decorative heel, which members being formed between the upper surface of the sole and the grounding surface, may be filled with an elastic material whose elastic character is weaker than the above members to put its appearance in good shape.

FIG. 1 is a sectional view showing a landing state in which the human heel receives a load. When the lower end of the human heel on the inner member 9 receives the load of 70 kg, it is depressed by a length of at least more than 2% of the whole length of the shoe. In this embodiment of the present invention, it is depressed by 5% thereof. In addition, a line connecting the front end 5 on the lower surface of the heel region and the lower surface 7 of the sole under the head of the metatarsus is lifted from an extending line (horizontal line) connecting the rear end of the lower surface of the grounding heel region and the front end 5 on the lower surface of the heel region by an angle of 12 degrees, which is caused by a difference in thickness from the upper surface of the sole to the ground at the heel region 4. More specifically, the rear portion of the heel region is thinner than a portion in the vicinity of the front end on the lower surface of the heel region (lower support 5). A state shown in FIG. 1, in which the human heel receives a load and the head of the metatarsus is lifted, is called the "first state".

The lifted angle of the head of the second metatarsus from the horizontal line is set at at least 5 degrees, preferably 6 and 7 degrees or more while the human heel is loaded. It is more preferable that the angle is wider. According to this embodiment of the present invention, the lifted angle is set to 12 degrees. According to an experiment, even if the angle is set to 8, 10, 15, 20 degrees or the like, its function is superior, apart from a fact that its appearance looks bad as the angle is increased.

According to this embodiment of the present invention, as the lifted angle of the head of the second metatarsus is increased, a line (hypotenuse) R4 shown in FIGS. 1 and 23 connecting the ankle and the lower end d of the calcaneus approaches the line x—x, whereby the "knee joint non-bending effect" can be obtained by the "supporting effect close to the vertical line", and a "knee stretching effect" to be described later is generated to prevent the wear of the knee joint. Thus, an effect to be described in [effect 1] later is generated.

In an experiment of this embodiment, the lifted angle is set to 12 degrees. If the angle is too small, the effect is reduced, and if the angle is too large, the effect is increased but its appearance becomes bad. Although a result obtained from 20 patients is based on when the present invention is applied, since a walking habit of the patient or the condition of the disease varies, the angle is selected according to the patients or the condition of the disease.

In addition, since the toe is lifted from the ground by bringing the lower end d of the calcaneus close to the vertical line x—x in order to obtain the "knee joint non-bending effect", the springs in the directions shown by the arrows A and B described in the above [Prior Art] are lost on the other hand and the "natural impact absorbing function" is lost. Thus, in order to compensate the loss, the heel region 4 is designed such that a height of the surface which is in contact with the lower end of the human heel is depressed by the above load, whereby the impact at the time of landing is absorbed. The impact absorbing mechanism is totally different from impact absorption in sports shoes or the like. More specifically, since the patient has a trouble in the knee and suffers from its pain, the patient walks in a quiet manner and lands on the ground with an almost static load as compared with people playing sports. It is preferable to provide a fine impact absorbing function to protect such vulnerable patients, so that the patient suffering from the pain each step can land on the ground more softly than healthy people. On the other hand, when a load is accelerated by velocity and applied to the sports shoes, for example, the load at the time of jumping becomes about four times as heavy as the weight. Since the impact absorbing mechanism in the sports shoe is designed so as to be elastically deformed by such strong force, it is not sufficiently elastically deformed by the quiet landing of the patient.

A structure which can be elastically deformed by such quiet landing will be described hereinafter.

More specifically, the human heel supporting elastic member 4a is made of a material which is easily elastically deformed and it is deformed from a state shown in FIG. 3(a) to a state shown in FIG. 1 when loaded. As the easily deformable material, a soft foamed material called E.V.A. (ethylene vinyl acryl) resin having hardness of 55 was used. In order to find how soft it is, when the material was picked by 10 mm×10 mm×10 mm and squeezed between fingers, it is easily compressed one fourth as small as the original size. This is exceptionally soft as a shoe material.

As can be seen by comparison between elasticity of the above soft material and elasticity at the heel region of the sports shoe, the heel of the sports shoe capable of bearing the load which is four times as heavy as the weight is never easily elastically deformed by such small static load. According to the present invention, when the human heel supporting elastic member 4a playing an important part in absorbing the impact at an initial stage of landing is about to be in contact with the ground, the weight is not yet loaded. When the weight is really loaded, since it is supported by the lower support 5 (in other words, the balance member 8), the load received by the human heel supporting elastic member 4a is reduced. Thus, the human heel supporting elastic member 4a can be made of the above-described extremely soft material against common sense in shoes.

In addition, when the inner member 9 disposed inside the shoe body is also made of an elastic material, the surface 9a receiving the human heel is also depressed a little and helpful to the impact absorption. Since a thickness of the inner member 9 is not so thick as that of the human heel supporting elastic member 4a, the impact absorbing function is not so great as of the human heel supporting elastic member, but it is considerably thick on the high side of the inclined surface as shown in FIG. 10, so that it is effective in the impact absorption. Thus, according to the embodiment shown in FIGS. 1 and 2, the inner member 9 is made of the elastic material and a degree of depression of the foot is measured by depression of the upper surface 9a of the inner member 9 positioned under the lower end of the human heel. In addition, the impact absorbing material may be partly substituted for the elastic material for the impact absorption according to the necessity in any embodiment described above.

Since it is preferable that a mechanism for absorbing the impact of the heel portion 9a on the surface of the inner member 9 can compensate the loss of the above-described "natural impact absorbing function given to a human being", when the human heel supporting member 4a is made of a sufficiently elastically deformable material. For example, in a case where a static load received by the surface 9a of the inner member 9 under the human heel is 70 kg, the total length of the shoe is set to 250 mm and a depressed length is set to 12.5 mm, which is 5% of the total length of the shoe, in this embodiment of the present invention. The depressed length was set to 2%, 3%, 4% and 5% of the total length of the shoe. As the depressed length is increased, the impact absorbing function becomes better. Therefore, although there is not limit until about 10%, it is set to at least 2%, if possible 3% or more, preferably 4% or more. The patients say that almost satisfied impact absorption can be obtained at 5% in this embodiment of the present invention.

Although the result obtained from 20 patients is based on when the present invention is applied, since a walking habit or the condition of the disease varies according to the patients, the depressed length is selected according to the patients or the condition of the disease.

The fact that the inner member 9 is made of the elastic material as described above greatly contributes to the impact absorption. Thus, the inner member 9 was made of the elastic material and a numerical value of depression was designated by a depressed value of the surface of the inner member 9 in this embodiment of the present invention. However, since the inner member 9 is exchangeably inserted into the shoe, which has a special purpose and configuration, so that the inner member 9 is sometimes treated as an exchangeable member which is separately sold in a stage of distribution. When the footwear is distributed without the inner member, since the depressing function can not be designated by the depressed value of the surface of the inner member under the human heel, it may be measured at the rear end of the upper surface of the sole. In this case, since there is no compressed deformation of the inner member 9 itself, the depressed value is small. As the value is increased, the impact absorbing function becomes effective, which is set to at least 0.5% or more, preferably 1.5% or more of the total length of the shoe. It was set to 2.5% in this embodiment of the present invention. In addition, the above value is set in a case where there is no inner member.

Additionally, there is a difference in elastic deformability between the human heel supporting elastic member 4a and the balance member 8, whereby the human heel supporting elastic member 4a is easily deformable more than the balance member 8. The difference is generated by at least one of a difference in size of pores, perforations, space and concave parts, a difference in number thereof, a difference in sectional area and a difference in materials.

Figure 4:
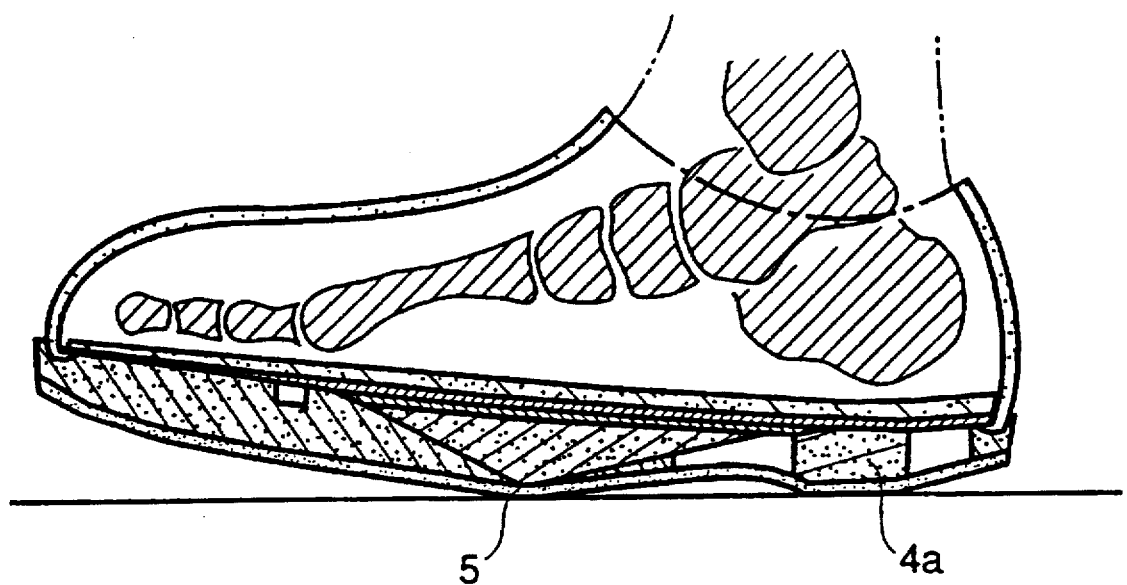
FIG. 4 is a vertical sectional view taken along line 3a—3a of FIG. 3(c) showing a modification of the footwear for patients suffering from the osteoarthritis of the knee according to the first embodiment of the present invention.

In addition, the lower surface of the sole between the rear end of the heel region and the lower support is called the lower surface of the heel region hereinafter, and it is preferable that that part is a substantially straight line or bent upward in its side view when loaded. For example, as shown in FIG. 4, the heel region according to a modification is bent upward. In a case where it has to be formed to protrude downward for reason of its design, at least one of the pores, perforations, space, concave parts and a soft material is provided in the heel region so that the heel region is easily bent, whereby the heel region substantially becomes in line in its side view when loaded (not shown). Thus, the heel region is formed substantially in line as shown in FIG. 3(a), or it is deformed upward as shown in FIG. 4, or it is formed so as to be easily deformed. Consequently, both the rear end on the lower surface of the heel region and the lower support 5 are in contact with the horizontal line and stable in the front-to-rear direction, so that it never rocks. In this respect, the footwear of the present invention largely differs from the rocker shoes described in the conventional example 3.

FIG. 2(a) shows the "second state", which is moved from the landing start state, in which the weight is gradually moved to be supported by the lower support 5 positioned at the front end on the lower surface of the heel region. The weight is mainly applied to the calcaneus 20 and the head of the metatarsus 30, which is supported by the balance member 8 comprising the horizontal member 6 and the support member 3a so as to concentrate on the lower support 5.

Since the whole weight of the patient, for example 70 kg if the patient weighs 70 kg is supported in a balanced manner unlike the normal shoe, the horizontal member 6 is disposed from the calcaneus 20 to the head of the metatarsus so as to bear the weight. Since the function of the horizontal member 6 is improved by the support member 3a, the function of the horizontal member 6 is regarded to be integrally formed with the support member 3a to be described later, which supports the load in the shape of T or the shape of an inverse triangle. That T shape or the inverse triangle is not always symmetrical about the lower support and the lower support is mostly on the forward side. The horizontal member 6 and the support member 3a are called generically as the balance member 8 hereinafter. The balance member 8 has a strength such that depression of the lower surface 7 of the sole under the head of second metatarsus 30 may not exceed 5 mm when the load of 15 kg is supported by the balance end portion at the head of second metatarsus 30. Preferably, it is less than 4 mm. According to this embodiment, the depression is within 3 mm when loaded. In addition, although the horizontal member 6 and the support member 3a are employed as a member contributing to the strength of the balance member 8, the strength of the balance member 8 is increased by forming an inner sole 3 m made of a hard material which extends close to the second metatarsus.

Additionally, according to this embodiment of the present invention, the position of the lower support 5 is set to a place of 50% of the total length of the shoe body measured from the rear end of the shoe body along a line connecting to the head of the second metatarsus. A ridgeline along the lower support 5 on the lower surface of the sole is formed such that the fifth toe side (the lateral side of the shoe) is disposed forward as compared with the first toe side (the medial side of the shoe) as shown by a line 5—5 of FIG. 3(c).

Although the support member 3a is formed between the lower support 5 and the longitudinal member 6 so as to consist the balance member 8. The support member 3a and the longitudinal member 6 are not necessarily separately formed and they may be integrally made of the same material for the purpose of reducing manufacturing costs.

If the depression of the balance member 8 is increased, the balance function is lost. Although the loss caused by the depression may be compensated by increasing a distance between the lower support 5 of the balance member 8 and the upper part of the balance (a height of the balance point), if the support member 3a is high, it looks bad in view of the design. If the appearance can be ignored, the depression may exceed 5 mm and the support member may be heightened. The value of the depression is measured assuming that the load is applied only to a place of the head of the second metatarsus 30. Actually, the value of the depression is not so great because the load does not concentrate on one point and the weight is supported by the whole of the sole. Although the value of the depression is set to within 3 mm assuming that the load is applied to one point in this embodiment, the depression is preferably more small if possible. Although the value of the depression is based on a result obtained from 20 patients when the present invention is applied, since a walking habit or the condition of the disease varies according to the patients, the depressed value is selected.

It is preferable that the balance member 8 is made of a material which is not likely to be elastically deformed as compared with the human heel supporting elastic member 4a.

Still further, a modification in which the structure is simplified for the purpose of reducing the manufacturing costs will be described. According to the modification, the front sole elastic member 3, the support member 3a and the human heel supporting elastic member 4a are made of the same material, which is shown in FIG. 5(a) and (b).

Figure 5A:
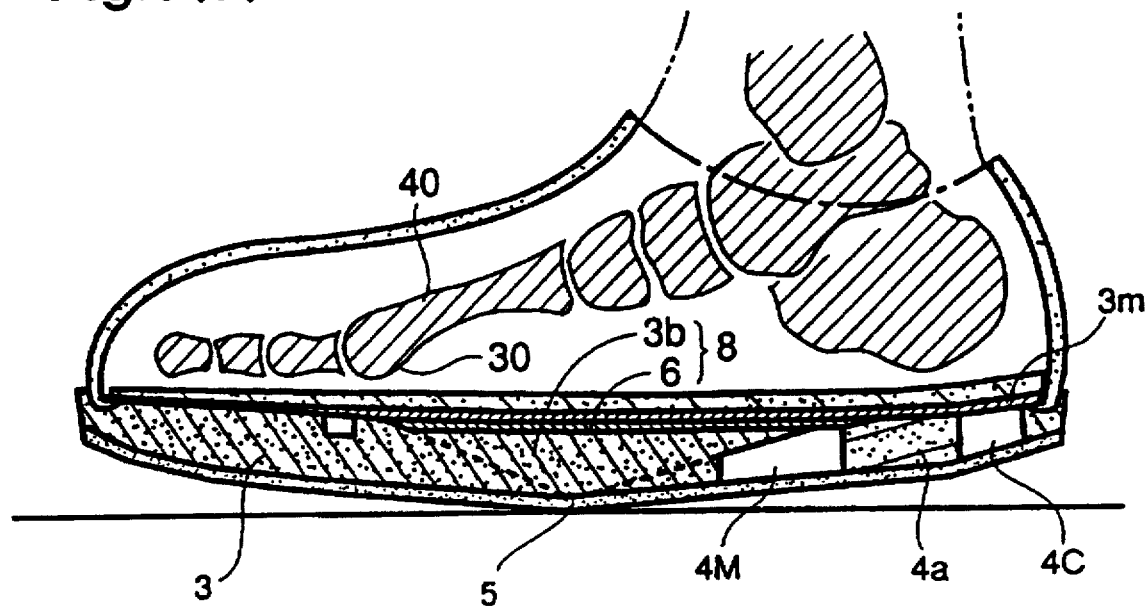
FIG. 5(a) and 5(b) are a vertical sectional view taken along line 3a—3a of FIG. 3(c) (FIG. 5(a)) showing a modification of the footwear for patients suffering from the osteoarthritis of the knee according to the first embodiment of the present invention, and a horizontal sectional view (FIG. 5(b)) showing a bottom part of the footwear just above a bottom covering material.
Figure 5B:
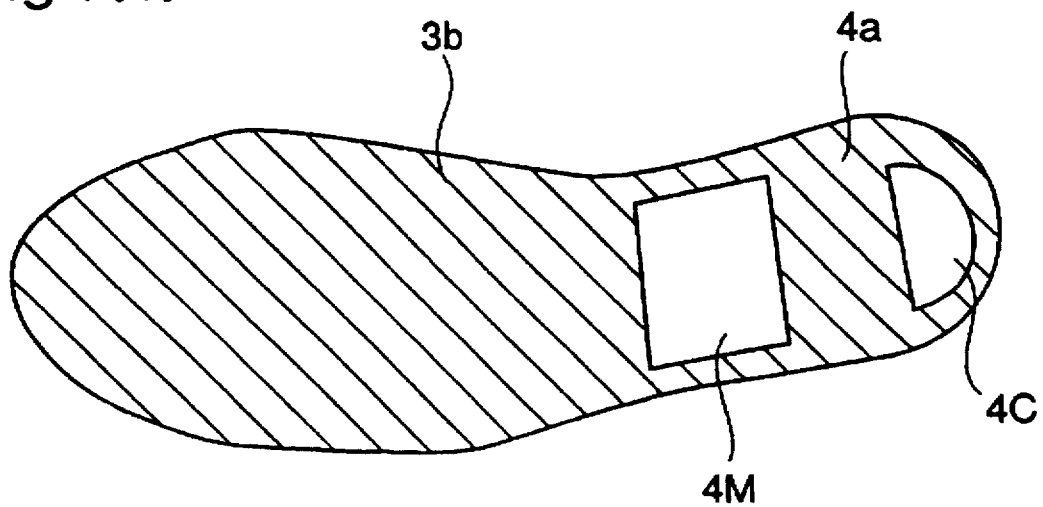

Referring to FIG. 5, the support member part 3b corresponding to the support member 3a in the above embodiment is integrally made of the same material as of the human heel supporting elastic member 4a. However, as shown in FIG. 5(a) and (b), there is a difference in elastic force between the support member part 3b and the human heel supporting elastic member 4a because of a difference in sectional area. In other words, the support member part 3b is formed without providing space, while the human heel supporting elastic member 4a is small in section because of spaces 4C and 4M. Therefore, the support member 3b is not likely to be elastically deformed as compared with the human heel supporting elastic member 4a. However, the support member 3a shown in FIG. 2 has a function of reinforcing the strength of the balance member 8 other than the function of serving as a support which is not likely to be deformed as compared with the human heel supporting elastic member 4a, so that in a case where the support member part 3b is made of the same material as of the human heel supporting elastic member 4a, it is preferable that a sufficiently hard material is used in the longitudinal member 6. In order to reduce the manufacturing costs, the longitudinal member 6 may be omitted and the inner sole 3 m having sufficient hardness may be substituted for the longitudinal member 6. According to the modification shown in FIG. 5, the lower support 5 is likely to be deformed when loaded and a position of the lower support 5 is unstable. When the position of the lower support 5 is unstable, the support is shifted according to the advance of the lower limb and the lower support 5 is shifted forward, which makes it difficult to walk (a problem of shifting of the support will be described later). Therefore, it is not very preferable that the support member part 3b is made of a soft material. However, when the support member 3b and the human heel supporting elastic member 4a are made of the same slightly hard material in order to prevent the shifting of the support, the human heel supporting elastic member 4a is not sufficiently elastically deformed. In order to prevent the problem, the sectional area of the human heel supporting elastic member 4a is reduced (by providing space) to be easily elastically deformed in this embodiment of the present invention.

Figure 19:
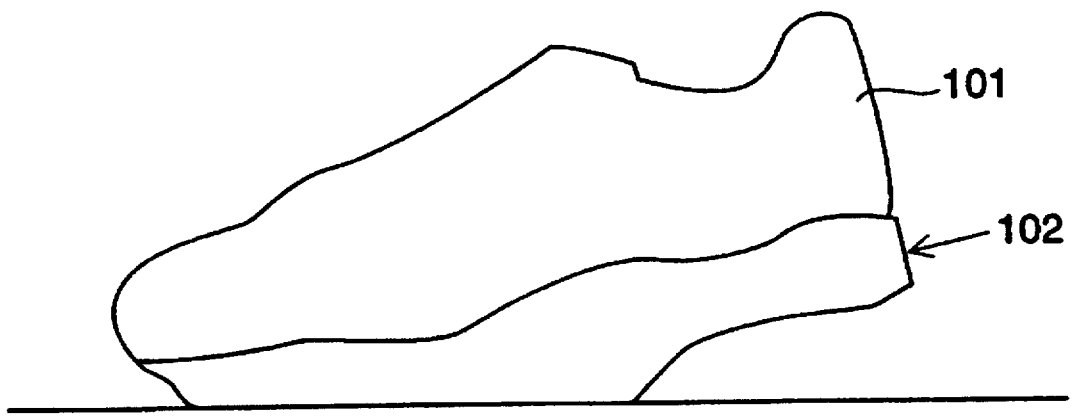
FIG. 19 is a side view showing an external appearance of a conventional shoe.
Figure 21:
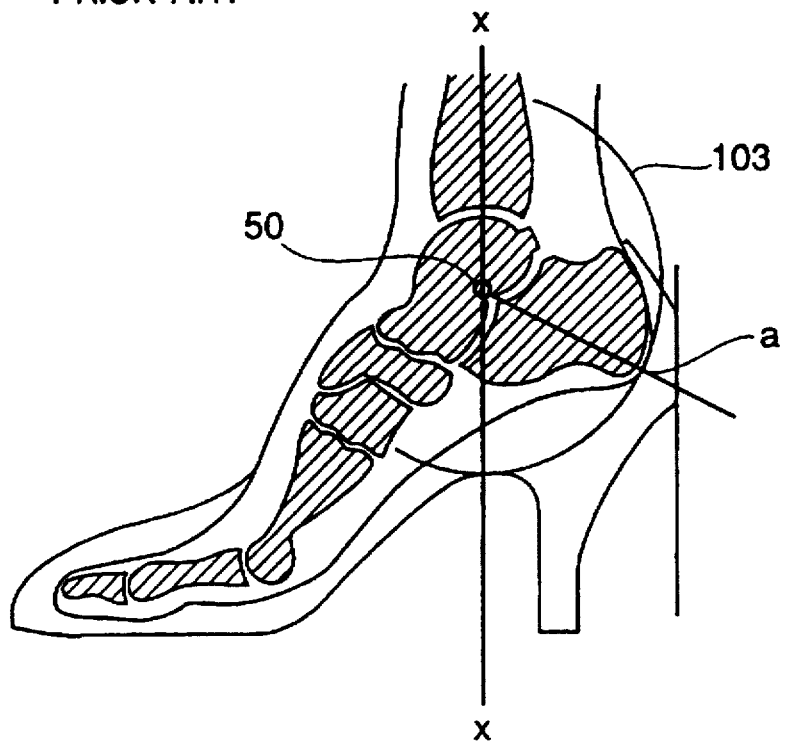
FIG. 21 is a view for explaining an action of a conventional high-heeled shoe.
Figure 22:
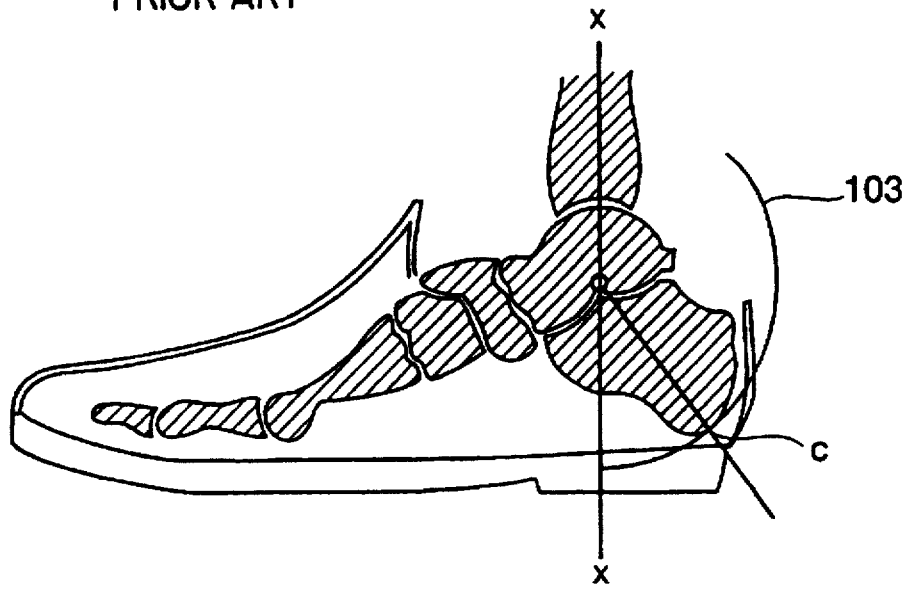
FIG. 22 is a view for explaining an action of a conventional low-heeled shoe.

In addition, the lower support 5 is placed at a position of 50% of the total length of the shoe, which is measured from the rear end of the shoe body. As a matter of fact, 40% may be enough if a doctor explains its function well for the patients and the patients understand the explanation of the doctor enough so that they can appropriately land on the ground from the human heel during walking. However, there are some patients who can not understand the explanation of the doctor and walk "on toes" as shown in FIG. 19 (conventional example). Those patients are mostly young and have muscular power. In order to prevent the above incorrect use, the lower support 5 was set more forward. The position of the lower support 5 was set to 41%, 43%, 45% or 47% as a trial and it was found that the incorrect use is reduced as the value is increased. Since the position was set to 50% in an experiment, there is no incorrect use with a few exceptions. Then, the lower support 5 was set to 55%, 58%, 61% or 63% as a trial. As a result, the incorrect use is reduced as the value is increased and the knee stretching effect is improved, but the patients complain that they easily become fatigued from long-distance walking because the knee is forcibly stretched. Even if the patients endure it as much as possible, when the value is more than 65%, the aged patients complains that the fatigue is too much to walk. Therefore, the position of the lower support 5 is decided according to the patients and conditions of the disease.

FIG. 3(c) is a bottom view showing the sole of the footwear according to this embodiment of the present invention. Generally, according to a structure of a normal shoe, a point leaving the ground is curved upward at the front portion. The leaving point is positioned with a distance from the rear end of the heel. The distance of fifth toe is shorter than that of the first toe because the fifth toe is most short.

In the present invention, however, the position of the lower support 5 is along the ridge line 5—5 crossing the lower surface of the sole as shown in FIG. 3(c), and the point on the ridge line on the fifth toe side is longer from the heel rear end than that on the first toe side, which is directly opposite to the normal shoe. Theory of the above was found in the course of trial experiments of the present invention. The theory is that the diseased part of the knee joint is less pushed up from the ground as will be described later in an embodiment 3 of the present invention. More specifically, when the balance member 8 is inclined forward as the lower limb is gradually advanced, the weight is supported by the ridge more on the fifth toe side positioned forward, and supported less on the first toe side positioned backward. Consequently, the load applied to the diseased side for the patients suffering from the bandy leg can be reduced. However, this theory is applied only to the patients of bandy leg and it is not used for the other patients.

Figure 2B:
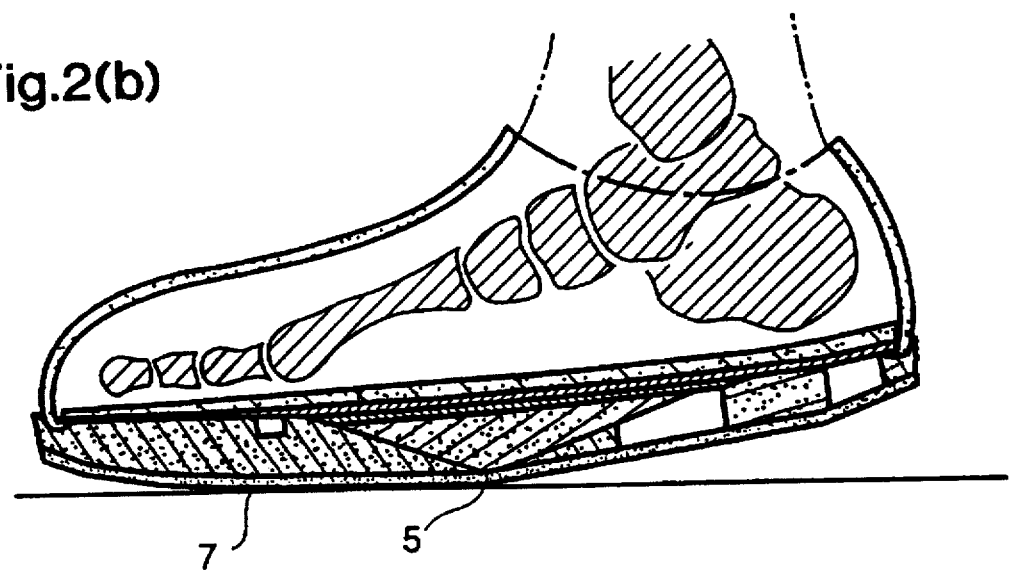

FIG. 2(b) shows the "third state" which is moved from the "second state". In the "third state", the weight is supported by a substantial straight line between the sole lower surface 7 under the head of second metatarsus and the lower support 5.

Since the position of the lower support 5 is almost in the center of the total length of the shoe and the foot is supported in a balanced manner, movement from the "second state" to the "third state" is only an action in which the balance is inclined, and there is low resistance therein.

Figure 6A:
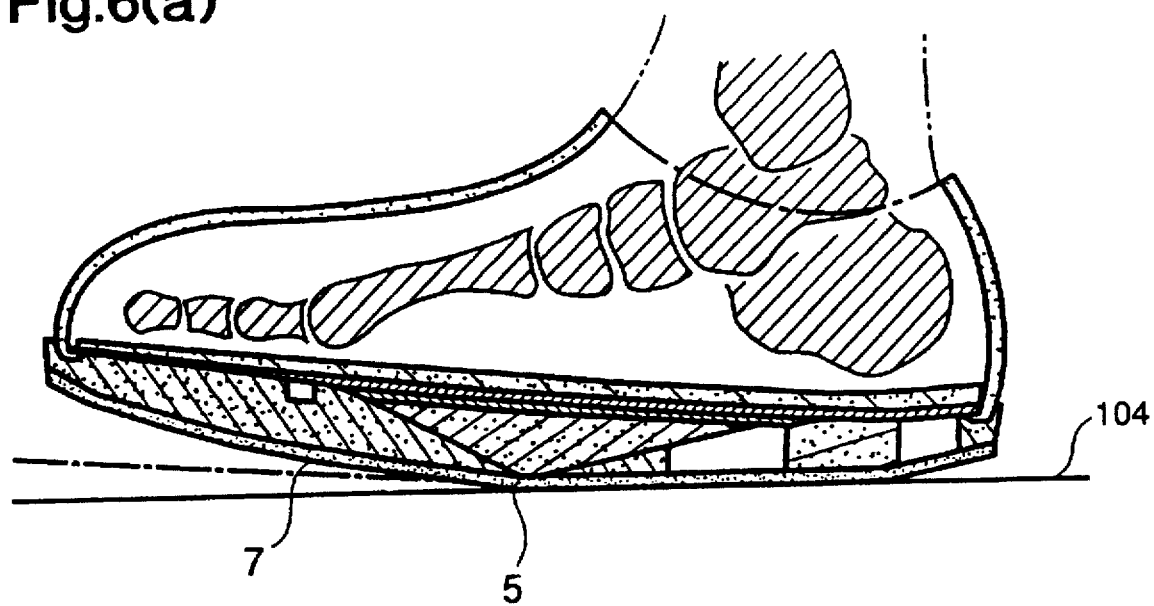
FIG. 6(a) and 6(b) are vertical sectional views taken along line 3a—3a of FIG. 3(c) (FIG. 6(a) and (b)) for explaining a function of the footwear for patients suffering from the osteoarthritis of the knee according to the first embodiment of the present invention.
Figure 6B:
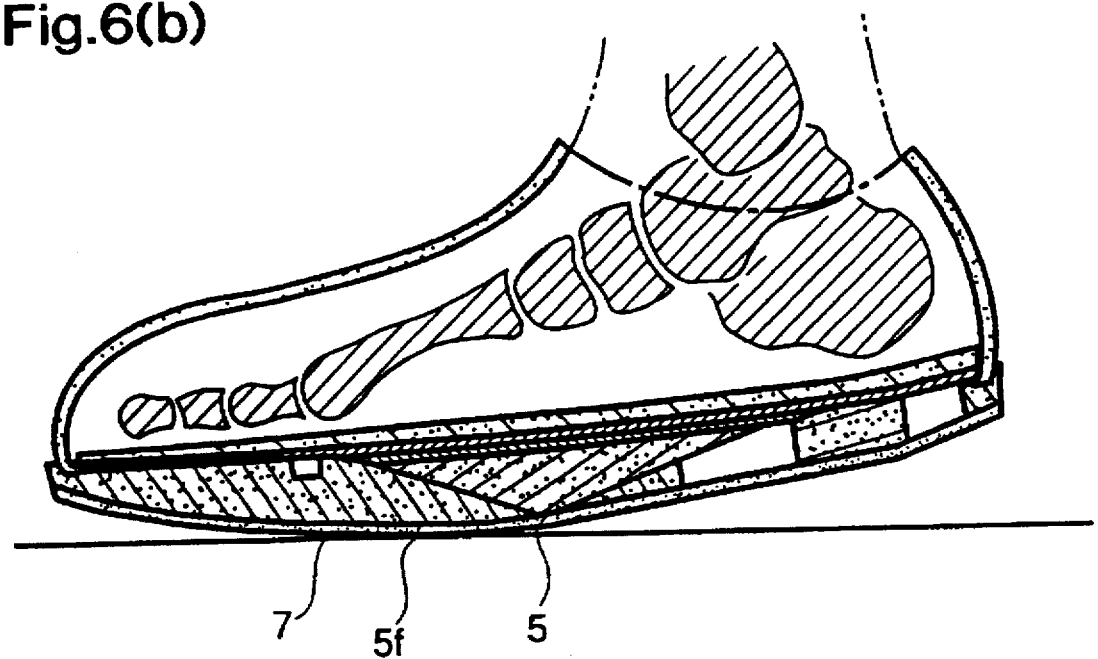
Figure 7:
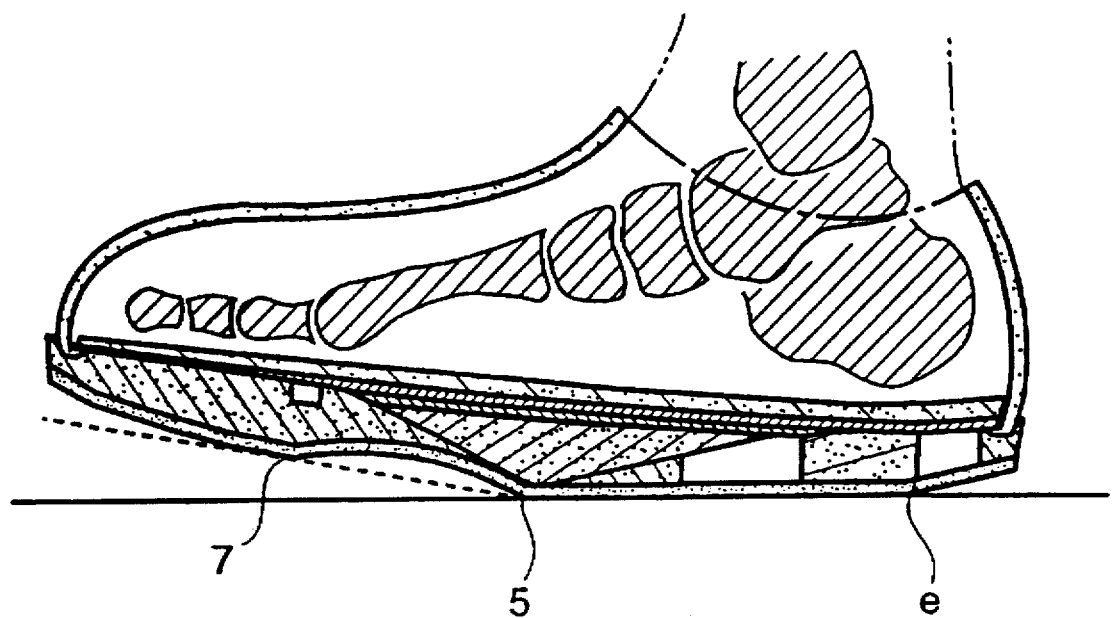
FIG. 7 is a vertical sectional view taken along line 3a—3a of FIG. 3(c) showing a modification of the footwear for patients suffering from the osteoarthritis of the knee according to the first embodiment of the present invention.

The reason why the resistance is low to move from the "second state" to the "third state" is that there is no resistance at the time of movement from the state shown in FIG. 2(a) to the state shown in FIG. 2(b) because the sole lower surface 7 under the head of the second metatarsus is connected to the lower support 5 substantially in line in side view shown in FIG. 2(b). If the line between the sole lower surface 7 under the head of the second metatarsus and the lower support 5 is slightly curved in side view as shown in FIG. 6(a) and (b), although the shoe looks better in view of design, the forward side of the lower support 5 functions as a gentle roller, so that the grounding position rolls to a point 5f as shown in FIG. 6(b) and it rolls further forward. Thus, the movement of the grounding position to the point 5f causes the same result as when the lower support 5 is shifted, which makes it difficult to walk. As described above, the position of the lower support 5 is set to the best position the doctor thinks, within a range from 41% to 65% according to requests and conditions of the patients. The best position is preferably never shifted. Thus, it is preferable that the line between the sole lower surface 7 under the head of the second metatarsus 30 and the lower support 5 is substantially straight or curved upward in its side view when loaded. A modification in which the line is curved upward is shown in FIG. 7. In addition, in a case where the line is curved downward for reason of its design as will be described later, it is preferable that at least one of the pores, perforations, space, concave parts, and a soft material is provided between the sole lower surface 7 and the lower support 5 so as to be easily depressed by the load to be the straight line shown in FIG. 2(b). Thus, since the support member 3a is not deformed, the forward part which is likely to be deformed as compared with the support member 3a is compressed by the load and deformed to a line, whereby the shifting of the lower support can be prevented. Thus, it has been confirmed by an experiment for the vulnerable people that the movement from the "first state" to the "third state" through the "second state" is an easy action in which only an inclination of the balance is changed, which is commonly applied to a case where the line between the sole lower surface 7 and the lower support 5 is made straight as shown in FIG. 2(b) by the load, a case where the line is originally formed like a configuration of FIG. 2(b), and a case where it is curved upward as shown in FIG. 7.

As shown in the figures, the lower support 5 has to functionally form an angular point so as to serve as a support. Although this angular point is an obtuse angle, the part of the angular point is likely to be worn away as compared with the other parts. In order to prevent that, the angular point may be shaped so as not be sharp within a range so far as the function as the support is not lost. If the angular point is not preferred, a decorative sole configuration forming member made of a soft material is buried in a part lifted forward from the angular point (lower support 5), and it may be deformed upward as described above in the "third state" when loaded. Since this is only the decorative member for the above purpose, it has to be made of a soft material which can be elastically deformed easily so that the fundamental function of the present invention may not be disturbed. The decorative member may be filled in the whole lifted part so that the lifted angle looks zero, or it may be filled in so that the lifted angle looks a certain degrees (for example, 3 degrees).

The state shown in FIG. 2(b) is a state where the balance member 8 is inclined forward, which is similar to a state where a normal shoe having a heightened heel. In that state, the heel is raised a little as compared with the first and second states. Since the state is opposite to a state where the Achilles' tendon is compulsorily stretched as described in the conventional example 1, the footwear can be gradually moved to the "fourth state" without stretching the Achilles' tendon. The "third state" which is prepared so as to be easily moved to the "fourth state" (kicking out) without stretching the Achilles' tendon is called "high-heel type of leaving-ground preparation state" hereinafter. Although the present invention is based on the principles in which the heel is low, the "high-heel type of leaving-ground preparation state" enables the Achilles' tendon not to be stretched on the low-heeled shoe which prevents or corrects a habit of grounding with the knee bent, which habit is peculiar to the patients of the normal osteoarthritis of the knee. Consequently, the footwear of the present invention is effective to prevent the worsening of the osteoarthritis of the knee and reduce pains.

Figure 2C:
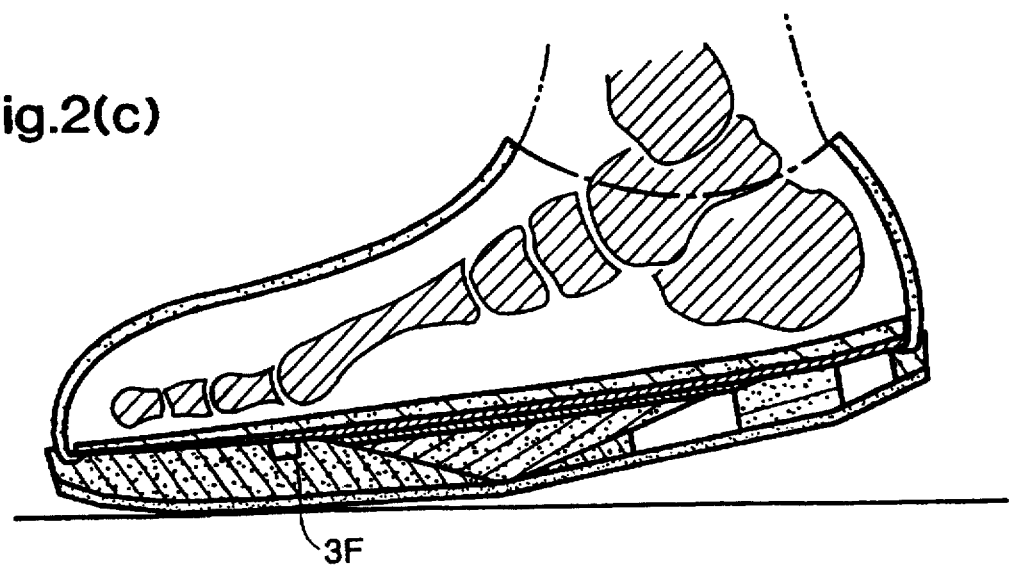

FIG. 2(c) shows the "fourth state", in which the weight is moved from the "third state" and the toe kicks off the ground. At this time, space 3F is provided so that the sole is easily bent, whereby the kicking-off can be easily performed.

Figure 23:
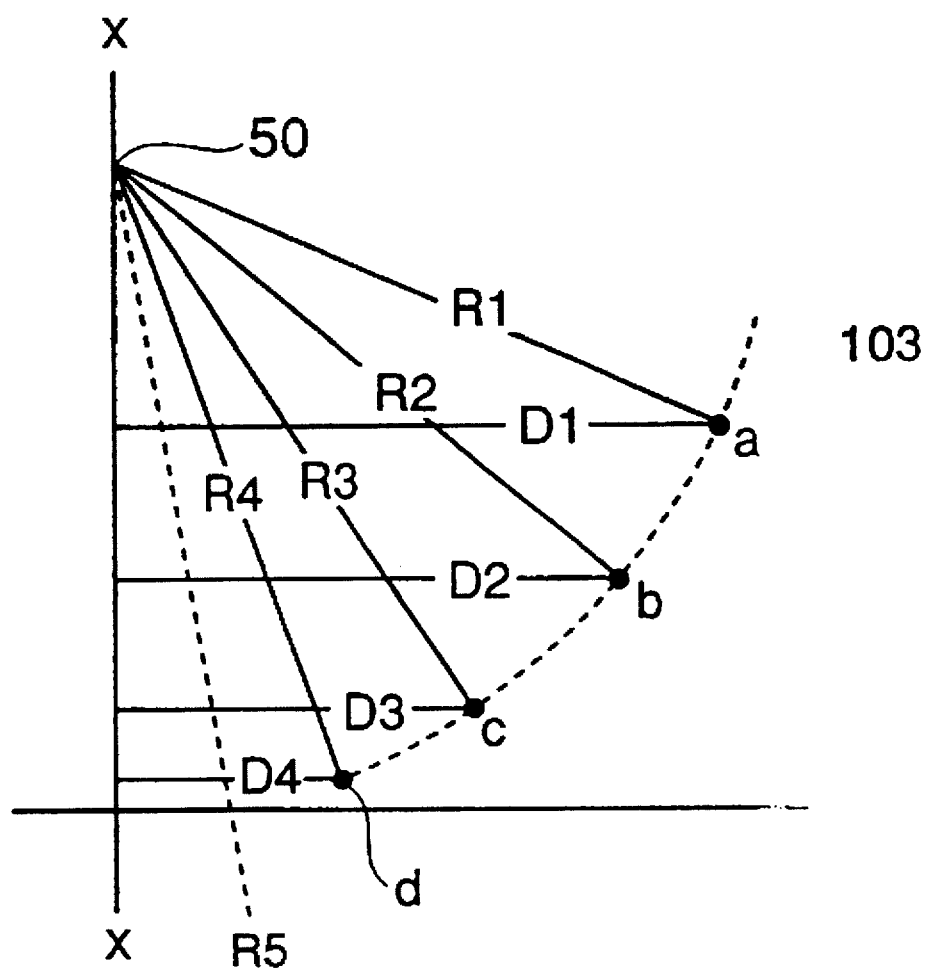
FIG. 23 is a view for explaining a theory of the footwear suffering from the osteoarthritis of the knee according to the first embodiment of the present invention.

According to this embodiment, when the landing is started, the sole lower surface 7 under the head of the second metatarsus is lifted from the horizontal line as shown in the "first state" in FIG. 1 and the height of the sole upper surface is extremely low at the rear end thereof, whereby the line connecting the center 50 of the ankle to the lower end d of the calcaneus (hypotenuse R4 shown in FIG. 1) approaches the vertical line x—x, so that the calcaneus lower end d can be close to the vertical line as much as possible as shown in FIGS. 1 and 23. The position d is lower than a position c (shown in FIG. 23) of the extremely low-heeled shoe described in the above. When a distance from the vertical line, in which, $$D = R \sin \alpha$$

is reduced as described in the [Problems that the Invention is to solve], bad force applied to the knee, that is, the "knee bending action by the calcaneus" can be reduced (which is called "supporting effect close to the vertical line").

When the landing is started in such state where the toe is lifted (a state where the front foot is still in the air), another effect is generated. When force of lowering the calcaneus is applied in a direction shown by an arrow G in FIG. 1 so that the sole under the head of the second metatarsus is lifted, the force is exactly opposite to the force of the above-described harmful landing impact (in the directions shown by the arrows A and B). Therefore, the force in the direction of the arrow G competes with the force of the harmful landing impact (in the direction of the arrows A and B) or acts so as to push back the harmful force, whereby beneficial force is generated when the landing is started. The "toe lifting effect" generated by the force in the direction of the arrow G is an auxiliary effect to the main effect of the above-described "supporting effect close to the vertical line" and they act on each other, whereby the "knee stretching effect" can be generated.

On the other hand, in order to compensate the natural impact absorbing function which was lost by the above "knee joint non-bending effect", the special impact absorbing structure is provided in this embodiment. Thus, while very appropriate impact absorbing force is applied to patients under the special conditions, the impact absorbing function can be applied to the vulnerable people beyond the natural impact absorbing function which is given to a human being, and the above "toe lifting effect" can be improved.

Then, the state is moved to the "second state" in which the whole weight is supported like a balance as shown in FIG. 2(a). At this time, since the strength of the balance member disposed in the sole is set so that depression of the balance member may not exceed 5 mm when the load of 15 kg is applied to the position of the head of the second metatarsus and a length of the longitudinal member 6 disposed above the balance member ranges from the calcaneus 20 to the head of the second metatarsus, the weight can be supported by the member in a balanced manner and the weight can be smoothly moved. In addition, since the lower support 5 is positioned almost in the center of the total length of the shoe in this embodiment, the position is in a dynamically less loaded state. Therefore, even the vulnerable people having poor muscle power can move from the "first state" to the "second state". Since the line between the lower support 5 and the sole lower surface 7 under the head of the second metatarsus is substantially straight, they can easily move to the "third state" without any resistance.

Figure 18:
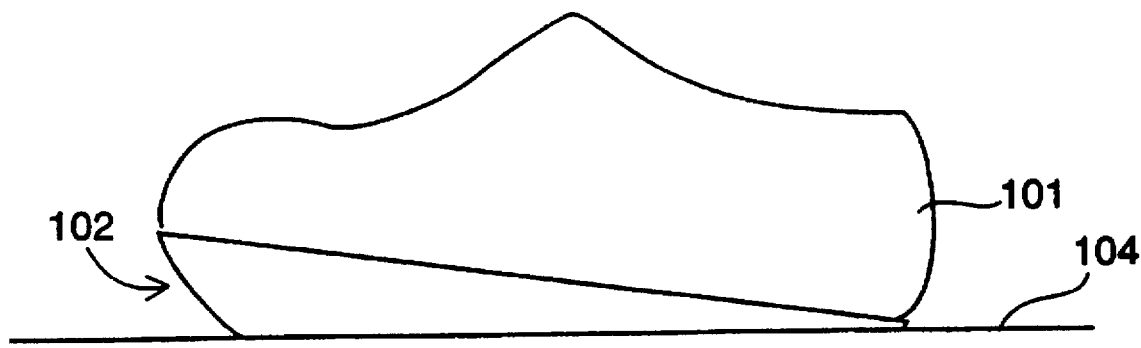
FIG. 18 is a side view showing an external appearance of a conventional shoe.

FIG. 2(b) shows the "third state", in which the weight is supported by the substantially straight line between the sole lower surface 7 under the head of the metatarsus and the lower support 5. The "third state" is close to a state in which a normal shoe having a heightened heel is put on and the person is released from the state in which the Achilles' tendon is stretched as described in the [problems that the invention is to solve]. Thus, since the state can be easily moved to the "third state", the Achilles' tendon is not forcibly stretched at the time of leaving the ground as described in the conventional example 1 shown in FIG. 18. Thus, even if the footwear is continuously used, the Achilles' tendon is not stretched as in the conventional example. Additionally, according to the present invention, the ideal lifted angle in the first state can be freely set to an appropriate value without regarding a problem caused by the unnatural stretching of the Achilles' tendon, whereby an ideal curing effect can be obtained. In addition, the calcaneus is lifted in the "third state" and the shoe state is easily moved to the next state of leaving the ground, that is, the "fourth state". Thus, the state which can be easily moved to the "fourth state" by heightening the calcaneus is called "high-calcaneus type of leaving-ground preparation state" hereinafter.

Furthermore, the bandy leg can be cured by advancing the ridgeline on the fifth toe side formed by the lower support 5.

FIG. 2(c) shows the "fourth state", in which the kicking-off is performed. The kicking-off operation can be easily performed by disposing the space 3F at a predetermined position forward from the sole under the head of the metatarsus because the sole is likely to be bent at the time of kicking-off.

In addition, although it is not directly related to the disease of the osteoarthritis of the knee which is an object of the present invention, there is a secondary merit. In addition to an improvement of a posture by the "knee stretching effect" of the present invention, the posture is further improved by curing the bandy leg (or knock knee) by advancing the ridgeline on the fifth toe side formed by the lower support 5 or by providing an inclined surface on the sole upper surface to be described later. Since energy is consumed a little to stretch the knee, a some shape-up effect can be also expected like the shoes shown in the conventional example 2. In common to these cases, the above-described defect which can not be avoided in the conventional examples 1 and 2 is solved by the present invention, and only the merit can be obtained.

Embodiment 2

Figure 8A:
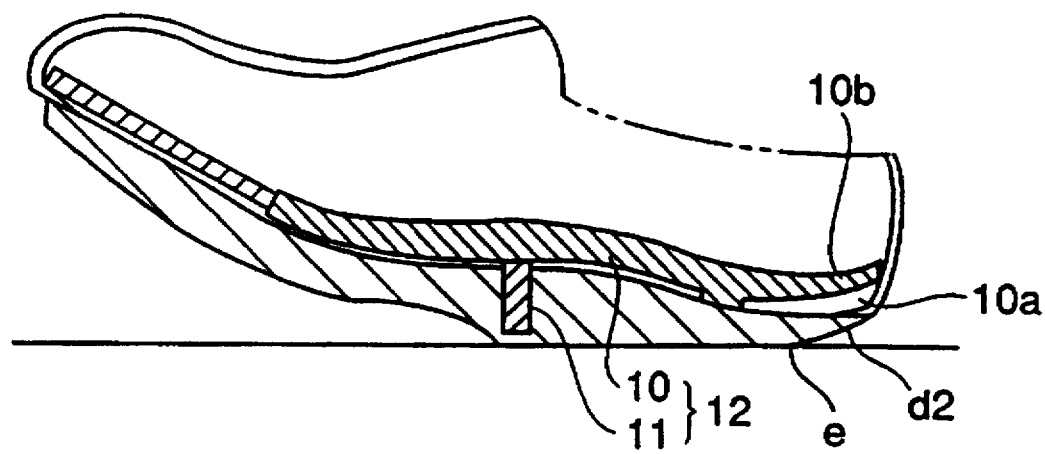
FIG. 8(a) and 8(b) are vertical sectional views (FIG. 8(a) and (b)) showing footwear for patients suffering from the osteoarthritis of the knee according to a second embodiment of the present invention.

Although the inner member 9 is made of the deformable elastic material in the embodiment 1 of the present invention, in order to provide a balance mechanism, the inner member 10 may be made of a material which is not elastically deformed so as to serve as the above longitudinal member 6 (shown in FIG. 1) as shown in another embodiment in FIG. 8(a) and (b). Referring to FIG. 8(a), a balance member 12 comprises a support member 11 (the support member 3a in FIG. 1) which is not substantially elastically deformed and an inner member 10 which is not substantially elastically deformed. Regarding to the impact absorbing mechanism, space 10a is formed by separating the rear end of the inner member 10 from the sole so that the heel region can be elastically deformed, which is the same as the case in FIG. 1. According to this embodiment of the present invention, instead of providing a decorative heel configuration forming member to be described later at a heel rear part, a slanting surface d2 is formed by diagonally cutting the heel rear part from a rear end e of the substantial heel so as to avoid hindrance to walk.

Figure 8B:
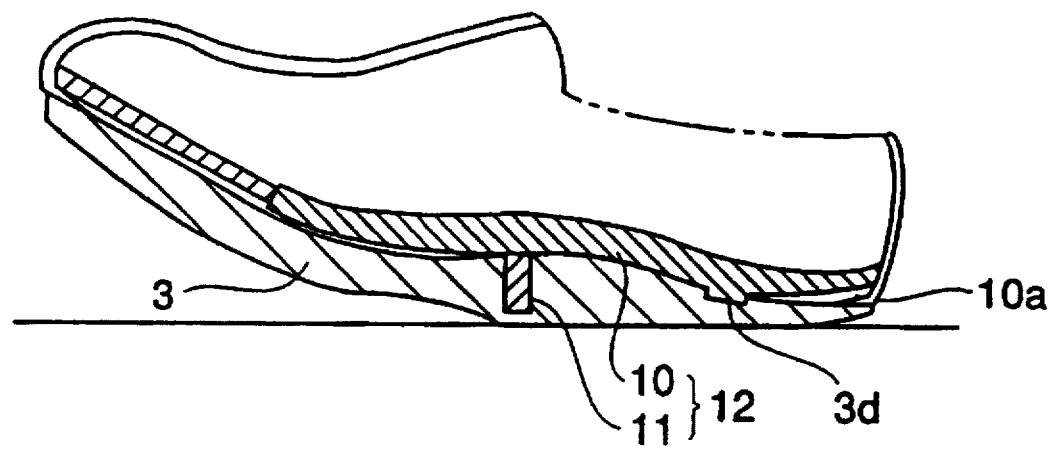

Since the longitudinal member 6 shown in FIG. 1 corresponds to the inner member 10 shown in FIG. 8 and the support member 3a shown in FIG. 1 corresponds to the support member 11 in this embodiment of the present invention, the same balance function is provided in FIGS. 1 and 8(a). As shown in FIG. 8(b), the inner member 10 depresses the sole 3d and falls when loaded and a rear part 10b of the inner member 10 falls to compress the space 10a, whereby the impact is absorbed. Since the inner member 10 is not elastically deformed according to this embodiment, there is a defect in which the member does not get fit the foot. In order to solve the defect, only a surface which is in contact with the foot may be made of the elastic member (not shown) within a range not to interfere the balance function.

Thus, since the balance mechanism comprises the inner member 10 and the support member 11 which are both not substantially elastically deformed, the inner member 10 can serve both as the longitudinal member 6 and the inner member 9 shown in the embodiment 1, whereby the same effect as in the embodiment 1 of the present invention can be obtained.

Embodiment 3

There will be described an embodiment 3 in which an inclined surface is disposed at the inner bottom of the shoe so as to cure the varus (valgus) in the shoe for the patients suffering from the osteoarthritis of the knee according to the embodiment 1, in addition to the effect of the above-described embodiments of the present invention.

Figure 9:
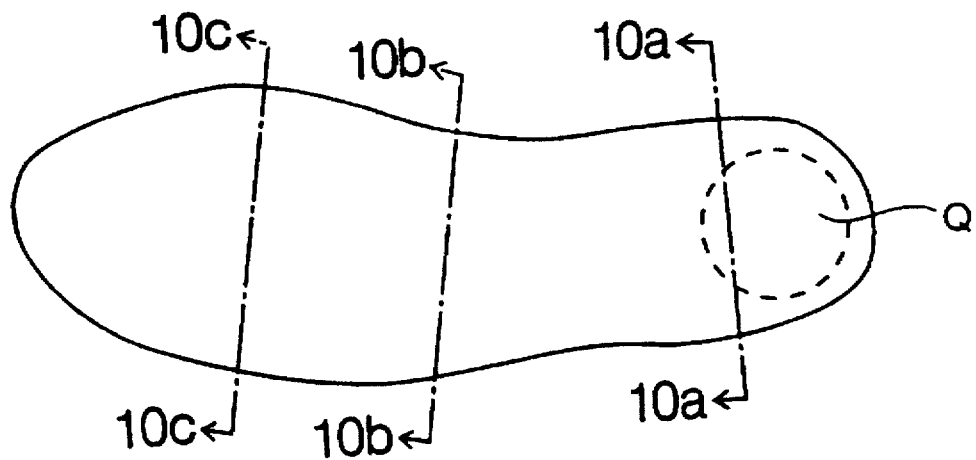
FIG. 9 is a plan view showing an inner member of footwear for patients suffering from the osteoarthritis of the knee according to a third embodiment of the present invention.
Figure 10A:
FIG. 10(a), 10(b), and 10(c) are sectional views (FIG. 10(a), (b) and (c)) of the inner member taken along a line a—a, a line b—b, and line c—c of FIG. 9, respectively.
Figure 10B:
Figure 10C:

FIG. 9 is a plan view showing the inner member 9 shown in FIG. 1, and FIG. 10(a), (b) and (c) are sectional views of the inner member taken along lines 10a—10a, 10b—10b, and 10c—10c of FIG. 9, respectively. The surface of the inner member 9 is inclined so as to be higher on the left than on the right when viewed from the rear side, so that the diseased side of the joint of the patient may be lower.

In order to prevent an upper on the lower side from being squeezed because the foot sideslips toward the lower side, the upper on the lower side is made of a reinforced material (not shown) as compared with the upper on the higher side.

Figure 11:
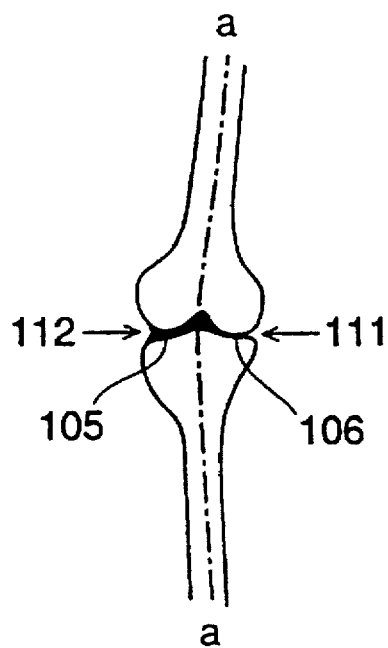
FIG. 11 is an explanatory view showing a joint of a patient.
Figure 12:
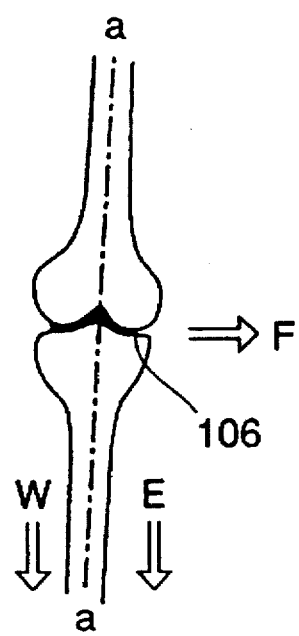
FIG. 12 is an explanatory view showing the joint of the patient.

The reason why the inclined surface is formed is well known, so that it is described briefly. A description will be given referring to the varus (bandy leg) as one example of the osteoarthritis of the knee. Referring to FIG. 11, since an alignment a—a is bent, an inner side 111 of the joint receives more load than a cartilage 105 on the outer side 112 of the joint and a cartilage on the inner side is worn away or lost. As a result, a bone is exposed, which is a diseased part 106. As means for curing the above, an inclined surface is provided in the shoe and the inner side of the joint is loaded in the direction shown by an arrow E because the one side is low and then, force in the direction shown by an arrow F is generated as shown in FIG. 12 so as to preferably relieve the load from the diseased part by correcting the alignment as shown in FIG. 12. Although there are some effect in the above means, the diseased part can not be desirably cured by the above means. Thus, the embodiment 3 and an embodiment 4 of the present invention solve the above problems.

Although the above was described referring to the example of varus, the outer side is replaced with the inner side and vice versa and the surface is inclined in the opposite direction in the above description in the case of valgus, whose description will be omitted.

Although the inclination of the surface is formed by the inner member 9 in this embodiment of the present invention, the inclination may be formed by the inner member 10 or the sole upper surface may be inclined. When the inner member 9 shown in FIGS. 9 and 10 is made of the elastic material, for example the above-described E.V.A. soft foamed material having hardness of 40 is used. In this case, since the elasticity of the inner member 9 acts together with the above-described human heel supporting elastic member 4a, the action is under the same concept. However, the both are functionally different.

The elasticity of the human heel supporting elastic member 4a has to be strong so as to bear the load of, for example 70 kg. The elasticity is so strong that, for example an impact between a rail and wheels in a railroad can be absorbed. Therefore, only when the weight of 70 kg is loaded by walking, the member is fully elastically deformed. However, the inner member 9 is preferably deformed by weak force (for example 1 kg) like a seat in the vehicle. The reason is that the human heel supporting elastic member 4a having strong elasticity is not deformed at the moment the landing is started because the weight of 70 kg is not fully loaded, and the inner member 9 which is deformed by the weak force absorbs the initial impact at the moment the landing is started. The initial impact at the moment the landing is started is most painful for the patient suffering from the knee. The weight of 70 kg loaded as static load after the moment of landing less influences the pain.

However, other than a function of absorbing the initial impact, the inner member 9 has to have another function of keeping the surface configuration inclined. The inclined surface must not be deformed by the weight.

Thus, the inner member has to have both functions of being soft so as to be elastically deformed by a slight initial impact such as 1 kg and of maintaining its configuration under the heavy static load of 70 kg.

The inner member 9 in the embodiment 3 shown in FIG. 9 has the inclined surface as shown in FIG. 10(a), (b) and (c). In this case, as compared with the human heel supporting elastic member 4a, the inner member 9 is largely in contact with the foot, so that a load per unit area is small in the inner member 9. Thus, such inner member 9 can be made of a soft material as compared with the human heel supporting elastic member 4a.

In addition, in order to provide both functions, a part shown by a region Q in FIG. 9 may be formed as a modification structure as will be described later. The region Q receives strong pressure from the human heel and also receives a load at the very beginning of the landing, so that it can absorb a small initial impact. Although the region is soft enough to be easily elastically deformed by even a load of 1 kg because of many pores (not shown in FIG. 9) as compared with another region, perforations, space, concave parts or the like may be disposed in the region Q instead of the pores or the region Q may be made of a further soft material than another part in the inner member 9.

Thus, according to the above structure, the configuration of the inclined surface is maintained while the small initial landing impact is absorbed, whereby the pain at the moment of landing which is mostly scared by the patient can be prevented.

In addition, the foot is prevented from sideslipping and squeezing the uppers by providing a stopper on the lower side of the inclined surface.

Embodiment 4

Although the effect of the inclined surface is sometimes not obtained contrary to expectation in experiments on the shoes according to the embodiment 3, the cause thereof is unknown. While the cause is investigated, the following is found out. More specifically, since the human heel supporting elastic member 4a is made of the extremely soft material, the human heel supporting elastic member 4a which supports the higher side of the inclined surface receives a more load and is more compressed than the human heel supporting elastic member 4a which supports the lower side of the inclined surface. Thus, when the higher side of the inclined surface is depressed more than the lower side thereof, force in the direction of an arrow W which is opposite to the force in the direction of the arrow E is generated as shown in FIG. 12, whereby force by which the alignment a—a is bent in the wrong direction shown in FIG. 11 is generated. Although this phenomenon can not be noticed without careful observation, this is a fatal phenomenon in the case where the human heel supporting member is made of the specially soft material. The human heel supporting elastic member 4a is not compressed equally on the right and left sides of the inclined surface and the human heel supporting elastic member on the higher side of the inclined surface is more depressed. This phenomenon is called a "unequal depression phenomenon of the heel" hereinafter.

According to this embodiment of the present invention, the above problems are solved as follows.

Figure 13:
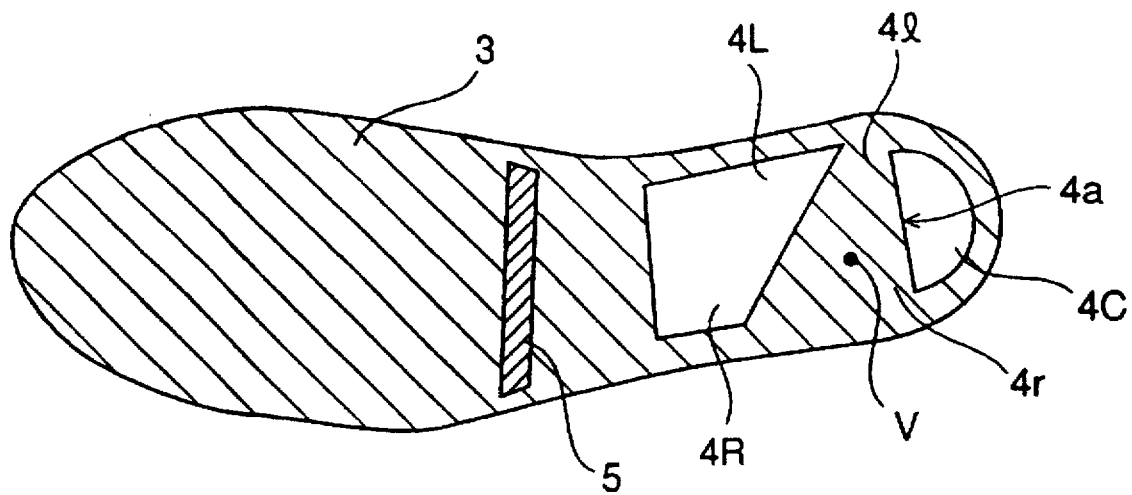
FIG. 13 is a horizontal sectional view showing a sole just above a bottom covering material of footwear for patients suffering from the osteoarthritis of the knee according to a fourth embodiment of the present invention.
Figure 14:
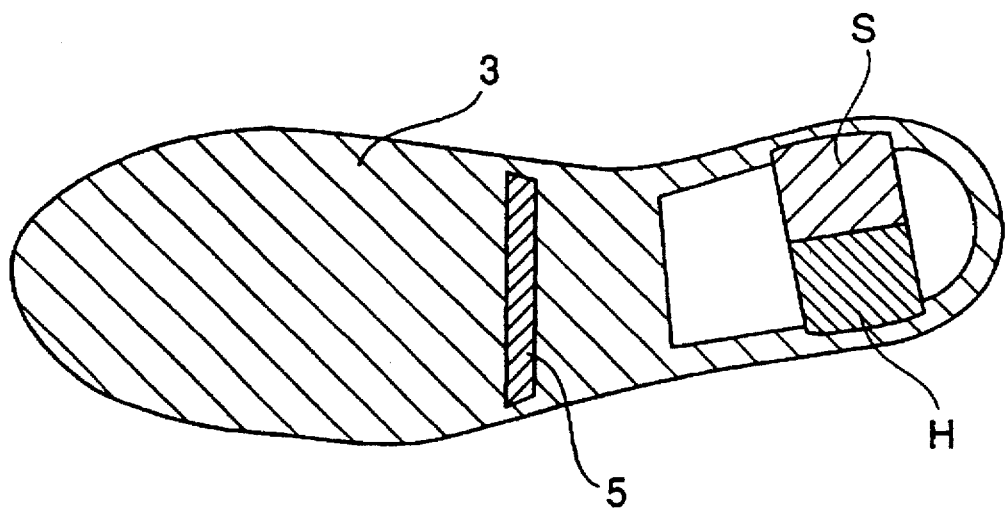
FIG. 14 is a horizontal sectional view of a sole just above a bottom covering material according to a modification of FIG. 13.

FIG. 13 is a horizontal sectional view showing the lowest surface of a sole and its vicinity according to this embodiment, which is cut at a height of 1 mm from the bottom covering material 3c. Referring to FIG. 13, the human heel supporting elastic member 4a has a smaller sectional area at a diseased side 41 and a large sectional area at an opposite side 4r. In other words, space 4L on the diseased side is larger than space 4R on the opposite side. Therefore, the diseased side is compressed by weak pressure. More specifically, the above-mentioned force in the wrong direction is prevented from acting to bend the alignment by adjusting their sectional area so as to provide a difference between the sectional areas 41 and 4r. Although there is a difference in size of the space in the above example, there may be a difference in size or number of the concave parts, pores or the like (not shown) instead of a difference in size of the space so as to enable the diseased side to be likely to be depressed. In addition, as shown in FIG. 14, the human heel supporting elastic member 4a may be made of a (soft) material S which is easily elastically deformed by weak force on the diseased side and made of a (hard) material H which is not likely to be deformed on the opposite side. Additionally, an intermediate material (not shown) may be disposed between the material S and the material H. Still further, the above means may be used together.

Thus, since the heel region comprises the human heel supporting elastic member 4a, the lost of the "natural impact absorbing function" is compensated by supporting the weight by the "soft human heel supporting elastic member" which is a basic structure of the present invention. While the "unequal depression phenomenon by the heel" which is inevitably generated by disposing the inclined surface in that case is prevented, whereby the angle of inclination of the inclined surface can be exactly maintained.

Embodiment 5

According to the embodiments 1 to 4, the position of the rear end e of the human heel supporting elastic member 4a which is a substantial part for supporting the weight was disposed at a position of 10% of the total length of the shoe from the rear end thereof. In addition, the decorative heel configuration forming member was disposed in the rear cut-out part of the human heel supporting elastic member 4a.

Figure 15:
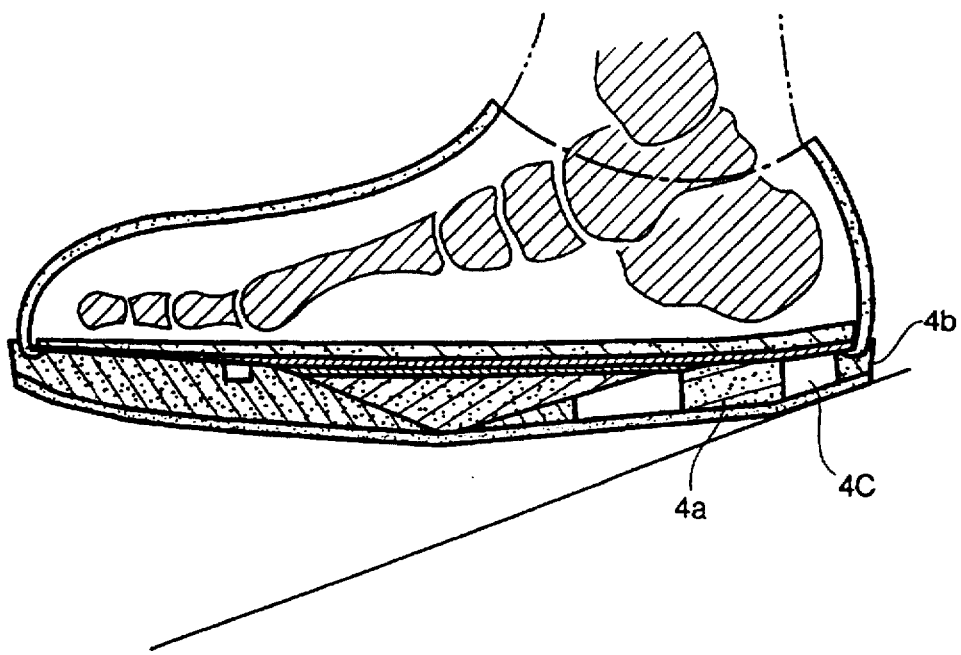
FIG. 15 is a vertical sectional view showing footwear for patients suffering from the osteoarthritis of the knee according to a fifth embodiment of the present invention.

FIG. 3(a) shows the state where the weight is not loaded. The human heel supporting elastic member 4a is designed with a previously calculated elastic material and a previously calculated configuration so as to support the weight at the heel portion at the landing. Then, in the state where the weight is supported after the landing, the elastic member 4a is compressed as shown in FIG. 1. According to this embodiment of the present invention, however, as shown in FIG. 15, the decorative heel configuration forming member 4b is formed in the rear portion of the human heel supporting elastic member 4a and the decorative heel configuration forming member 4b is made more deformable than the human heel supporting elastic member 4a in order not to affect the supporting of the weight. As a result, the "knee bending action by the calcaneus" described in the conventional example is reduced. Consequently, the "knee bending action by the calcaneus" shown in FIG. 20(b) is prevented.

Although the decorative heel configuration forming member 4b is easily deformed by making the space 4C large in this embodiment, the same effect can be obtained if the member 4b is made of the same material as in the human heel supporting elastic member 4a by increasing the concave parts or pores (not shown) instead of the space 4C, or it may be made of a material softer than the human heel supporting elastic member 4a. It is preferable that the rear side from the position e shown in FIG. 3(a) is formed so as to lift from the ground as shown by a lifting inclined surface d1 in the figure. In addition, as its modification, as shown in FIG. 8(a) and (b), an inclined part d2 may be formed by cutting out the rear side from the rear end e of the human heel supporting elastic member 4a.

Figure 16:
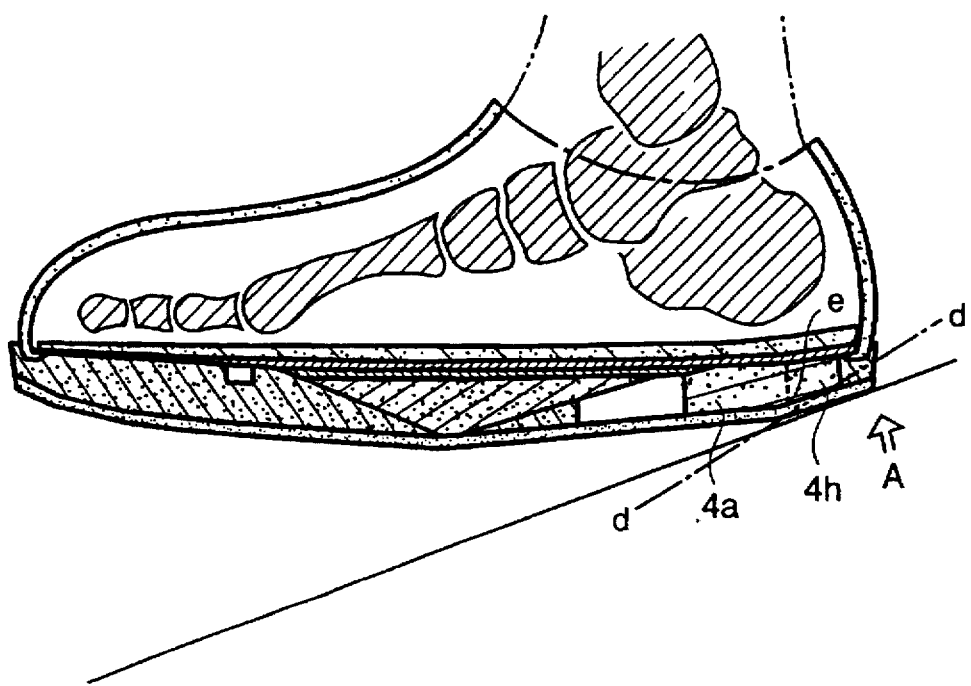
FIG. 16 is an explanatory view showing an action of FIG. 15.

FIG. 16 is a view for explaining an action of the decorative heel configuration forming member 4b shown in FIG. 15, in which the space 4C (shown in FIG. 15) of the decorative heel configuration forming member 4b is filled with a material 4h for convenience of explanation. If the person goes down a slope on the same condition as in FIG. 15 or lands on the ground with a heightened toe, since the space 4C does not exist, the above-described harmful force from the ground which is shown by an arrow A is generated at a part 4h, whereby the diseased part of the knee joint receives the impact.

The large space 4C is easily deformed in FIG. 15 as compared with FIG. 16 and counterforce from the ground is small, which is effective in not only going down the slope but also habitually landing with the heightened toe. If the ideal function is sought without regard to its appearance, it is better not to provide the decorative heel configuration forming members 4b and 4h. In addition, as a modification, even when the space of the decorative heel configuration forming member is filled with the elastic material as shown in FIG. 16, if the heel is more sharply cut out from a substantial heel rear end e toward the heel end along a dotted line d—d, although it looks bad in view of design, the effect similar to the "supporting effect close to the vertical line" can be obtained.

However, there is a difference in condition of a disease among patients and sometimes a complication sets in. To the aged patient who is unable to satisfactorily stand up for lack of a function of standing up, as described in FIG. 16, the lack of the function of standing up is sometimes compensated by a structure in which the heel rear portion 4h is filled in. Even in a case of the structure shown in FIG. 16, since the human heel supporting elastic member 4a is made of a sufficiently soft elastic material, the substantial supporting point is shifted forward, whereby almost the same effect as the "supporting effect close to the vertical line" can be obtained.

According to each of the above embodiments and modifications, the position of the lower surface rear end e of the human heel supporting elastic member 4a substantially supporting the weight is positioned forward from the rear end of the shoe body. The position is at a place of at least 5% of the total length of the shoe from the rear end of the shoe, preferably 6% to 7% or more. According to this embodiment of the present invention, the rear end e of the human heel supporting elastic member 4a is positioned forward by 10% from the rear end of the shoe body. Thus, by setting the rear end e of the human heel supporting elastic member 4a forward, the "knee joint non-bending effect" is further improved. More specifically, if the rear end e is put forward, the calcaneus lower end can be positioned so as to be close to the vertical line more than the hypotenuse R4 (shown in FIGS. 1 and 23).

Figure 17:
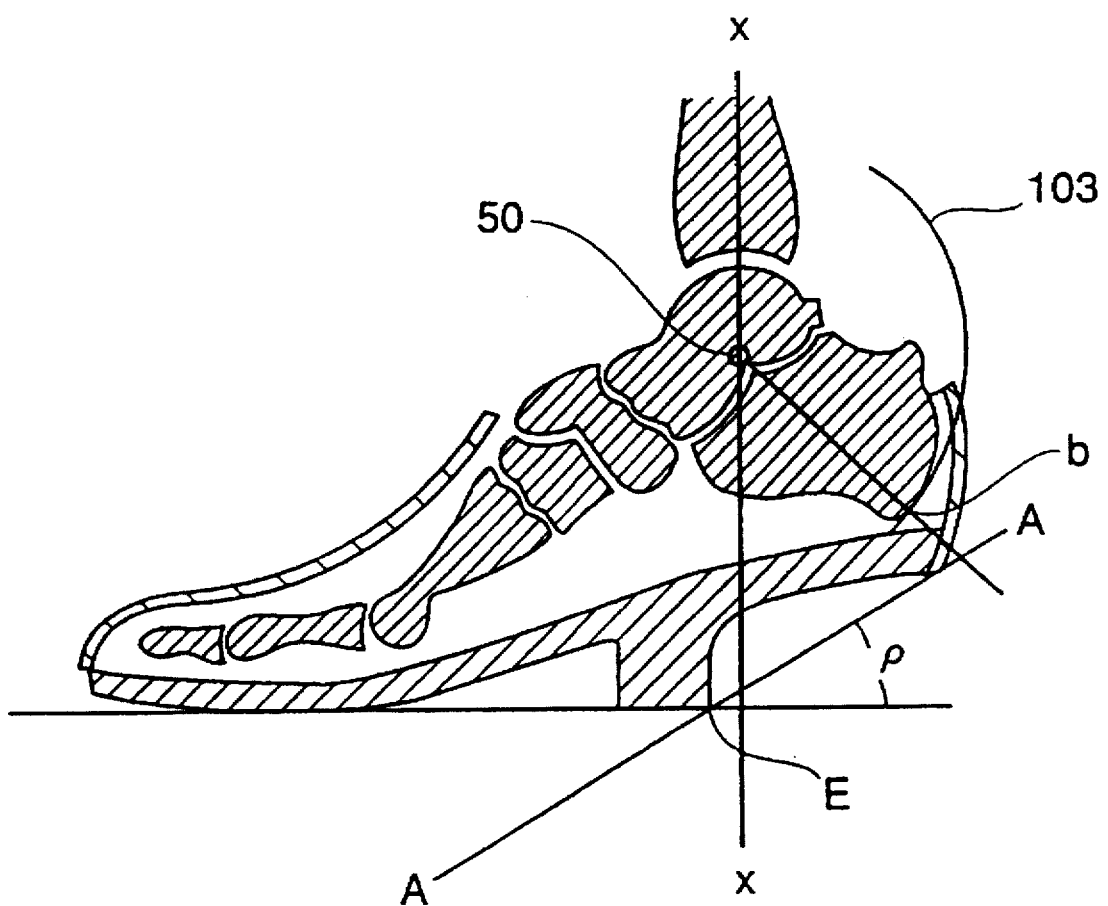
FIG. 17 is a vertical sectional view showing a shoe according to a previous application.

In addition, although the heel rear end E shown in FIG. 17 is made of a hard material and angular according to the previous application and the weight is collectively supported by the rear end E at the moment the landing starts. To the contrary, since the human heel supporting elastic member 4a is itself made of a soft material in the embodiment shown in FIG. 1, although the rear end e shown in FIG. 1 looks angular, it is actually easily deformed. Thus, since the weight is supported by the whole of the substantial heel 4a, it is thought that there is a substantial supporting point forward from the angular rear end e shown in the figure. The supporting point may be thought to exist in the vicinity of the center of gravity V of the human heel supporting elastic member 4a as shown in FIG. 13. When it is assumed that the hypotenuse R5 passes through the center of gravity V, the hypotenuse R5 is more close to the vertical line than the hypotenuse R4 as shown in FIGS. 1 and 23. Although the angle of the hypotenuse R5 is not decided, it can be expected the hypotenuse R5 surely exceeds the hypotenuses R1, R2, R3 or R4 shown in FIG. 23 to approach the vertical line x—x. Thus, the effect generated in the weight supporting state in which for example the hypotenuse R5 approaches the vertical line x—x is called the "supporting effect close to the vertical line".

Thus, when the rear end of the human heel supporting elastic member 4a serving as the substantial heel is positioned forward from the rear end of the shoe body, the hypotenuse R5 further approaches the vertical line x—x as described above, so that the weight is supported at a forward position from the rear end of the shoe body. Consequently, the harmful force shown by the arrow A (shown in FIG. 20) is prevented by the "supporting effect close to the vertical line" and the "knee bending action by the calcaneus" in the direction shown by the arrow B can be sufficiently prevented.

When the bottom covering material 3c is omitted, since the space or concave parts formed in the embodiments 1 to 5 are exposed and look bad, that parts may be filled with an elastic material whose elasticity is lower than the other parts in order to adjust the appearance so as not to look strange.

Embodiment 6

An embodiment 6 shows footwear which has functions described in the above embodiments of the present invention. In addition, the footwear is easy to put on and a configuration of uppers is changed so as to be usable indoors. In this embodiment, the footwear like a backless slipper is shown.

Figure 24:
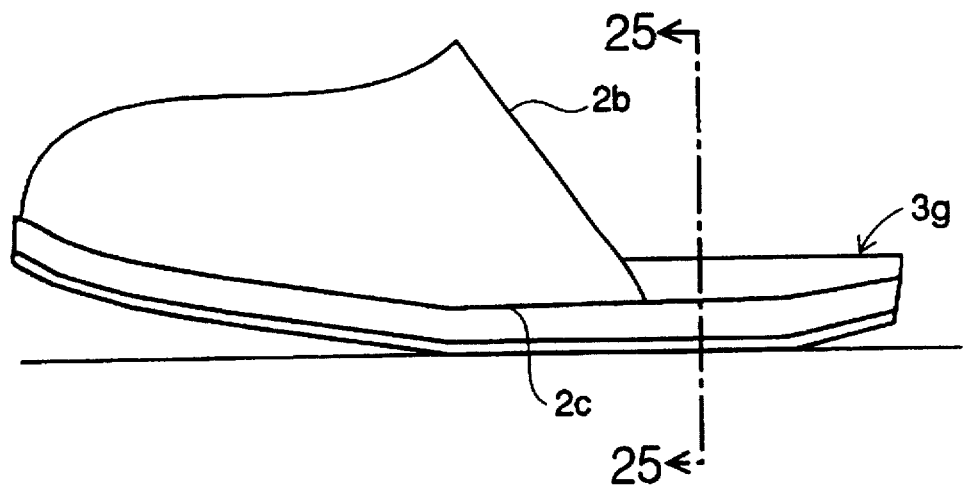
FIG. 24 is a side view showing footwear for patients suffering from the osteoarthritis of the knee according to a sixth embodiment of the present invention.
Figure 25A:
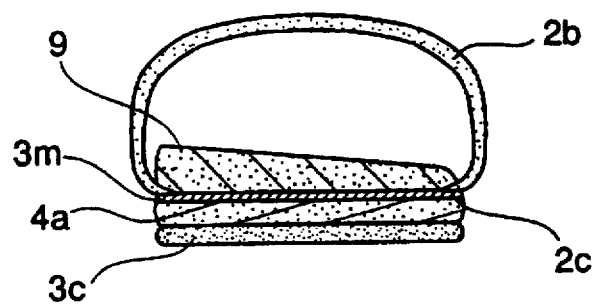
FIG. 25(a) and 25(b) are a sectional view (FIG. 25(a)) taken along a line 25—25 of FIG. 24, and a view (FIG. 25(b)) showing a modification of stitching.
Figure 25B:
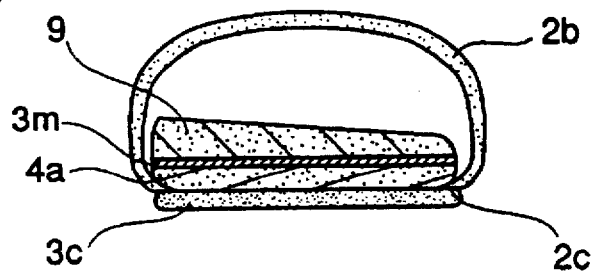

FIG. 24 is a side view showing the footwear according to the embodiment 6 of the present invention. FIG. 25 is a sectional view taken in a direction shown by arrows along a dotted line 25—25 of FIG. 24. The same reference numerals as in FIG. 1 are allotted to the same or corresponding parts. Referring to the figure, the inner material 9, the inner sole 3m, the longitudinal member 6, the calcaneus supporting elastic member 4a, the front sole elastic member 3 and the support member 8 which were described in the above each embodiment of the present invention are covered with a covering material (not shown) and they form a step-on part 3g. Reference numeral 2b designates uppers of the slipper and reference numeral 2c designates a lower end of the upper.

A sole member 3h exposing a foamed material formed of synthetic resin which is not covered with a covering material is disposed under the step-on part 3g. The step-on part 3g is joined to the sole member 3h. The lower end 2c under the upper 2b is stitched between the step-on part 3g and the sole member 3h. A stitching method of the upper 2b, the step-on part 3g and the sole member 3h, as shown in FIG. 25(a) and (b), comprises a method in which the uppers lower end 2c is stitched between the inner member 9 and the calcaneus supporting elastic member 4a, a method in which the uppers lower end 2c is stitched between the calcaneus supporting elastic member 4a and the sole member 3h or the like, but the stitching method is not limited to the above because the method has essentially nothing to do with the functions of the present invention.

Thus, since the configuration of the upper is like a slipper, there can be provided the footwear which is effective to patients suffering from the osteoarthritis of the knee because it is easy to put on and can be used indoors.

We claim:

1. Footwear for persons suffering from osteoarthritis of the knee comprising:

a foot support surface including a first portion for supporting a heel and a second portion for supporting a metatarsal region of a foot of a wearer of the footwear;

a balance member for supporting a weight of the wearer disposed beneath the foot support surface and having a ridge disposed between the first and second portions of the foot support surface in a lengthwise direction of the footwear; and a heel support disposed beneath the first portion of the foot support surface and being more readily compressed under a vertical load than the balance member, the first portion of the foot support surface sloping downwards in a transverse direction of the footwear from a first side to a second side of the footwear when a lower surface of the heel support is horizontal, the heel support being less compressible by a vertical load on the first side than on the second side of the footwear.

2. The footwear as claimed in claim 1 wherein the heel support has a greater horizontal cross-sectional area on the first side than on the second side of the footwear.

3. The footwear as claimed in claim 2 wherein the cross-sectional area is measured along a plane in a vicinity of the lower surface of the heel support.

4. The footwear as claimed in claim 3 wherein the plane is approximately 1 mm above the lower surface of the heel support.

5. The footwear as claimed in claim 1 wherein a length of the heel support in the lengthwise direction of the footwear decreases from the first side to the second side of the footwear.

6. The footwear as claimed in claim 1 wherein the heel support comprises a first material on the first side of the footwear and a second material softer than the first material on the second side of the footwear.

7. The footwear as claimed in claim 1 including an empty space adjoining a front side of the heel support.

8. The footwear as claimed in claim 7 wherein the space has a smaller horizontal cross-sectional area on the first side than on the second side of the footwear.

9. The footwear as claimed in claim 1 including a ground contacting surface disposed beneath the foot support surface and extending forward from the ridge of the balance member towards a front end of the footwear, wherein when the footwear is in an unloaded state and the ridge of the balance member and the lower surface of the heel support are in a common horizontal plane, the ground contacting surface slopes upward with respect to the horizontal plane beneath the second portion of the foot support surface.

10. The footwear as claimed in claim 1 wherein a rear end of the lower surface of the heel support is longitudinally spaced from a rear end of the footwear.

11. A method of supporting a foot of a person suffering from osteoarthritis of the knee comprising:

supporting a heel of a leg having a knee with a diseased side and a healthy side on a foot support surface disposed atop a heel support of footwear such that the foot support surface beneath the heel slopes downwards in a transverse direction of the footwear from a first side of the footwear corresponding to the healthy side of the knee to a second side of the footwear corresponding to the diseased side of the knee with a lower surface of the heel support horizontal, the heel support being less compressible by a vertical load on the first side than on the second side of the footwear.

12. A method as claimed in claim 11 including supporting the heel with a first material on the first side of the footwear and with a second material softer than the first material on the second side of the footwear.

* * * * *